United States Patent [19]

Stenzel et al.

[11] Patent Number: 5,028,711
[45] Date of Patent: Jul. 2, 1991

[54] BENZOPYRAN DERIVATIVES, PROCESSES FOR THEIR PREPARATION AND THEIR USE AND PREPARATIONS CONTAINING THE COMPOUNDS

[75] Inventors: Wolfgang Stenzel, Reinbek; Theo Schotten; Ben Armah, both of Hamburg, all of Fed. Rep. of Germany

[73] Assignee: Beiersdorf Aktiengesellschaft, Hamburg, Fed. Rep. of Germany

[21] Appl. No.: 376,328

[22] Filed: Jul. 6, 1989

[30] Foreign Application Priority Data

Jul. 12, 1988 [DE] Fed. Rep. of Germany ....... 3823533

[51] Int. Cl.$^5$ ................. C07D 405/04; C07D 407/04
[52] U.S. Cl. ..................... 546/196; 540/363; 540/524; 540/596; 544/6; 544/54; 544/62; 544/70; 544/96; 544/151; 544/155; 544/230; 544/315; 544/318; 544/331; 544/376; 546/15; 548/182; 548/186; 548/190; 548/193; 548/225; 548/229; 548/234; 548/300; 548/301; 548/316; 548/318; 548/407; 548/525; 548/950; 548/952; 548/958; 549/345; 549/387; 549/399
[58] Field of Search ............ 540/363, 524, 596; 544/376, 62, 151, 6, 70, 230, 315, 318, 331; 546/196, 15; 548/525, 950, 958, 182, 186, 190, 193, 229, 234, 300, 316, 318, 407; 549/345, 387, 399

[56] References Cited

U.S. PATENT DOCUMENTS 4,251,537  2/1981  Evans ................................. 544/376
4,366,163  12/1982 Evans et al. ......................... 544/62

FOREIGN PATENT DOCUMENTS 0028064  5/1981  European Pat. Off. .
0076075  4/1983  European Pat. Off. .
0093535  11/1983 European Pat. Off. .
0107423  5/1984  European Pat. Off. .
0120427  10/1984 European Pat. Off. .
0120428  10/1984 European Pat. Off. .
0126350  11/1984 European Pat. Off. .
0139992  5/1985  European Pat. Off. .
0207614  7/1987  European Pat. Off. .
0237138  9/1987  European Pat. Off. .
0273262  7/1988  European Pat. Off. .
2145319  8/1973  Fed. Rep. of Germany .
2828951  1/1979  Fed. Rep. of Germany .
3040727  8/1981  Fed. Rep. of Germany .
3703227  8/1988  Fed. Rep. of Germany .
3703229  8/1988  Fed. Rep. of Germany .
2346346  10/1977 France .

OTHER PUBLICATIONS

Chemical Abstracts, vol. 105, 1985, Abstract No. 190938u.
J. Medicinal Chemistry 29, 1986, pp. 2194–2201.
J. Medicinal Chemistry 27, 1984, pp. 1127–1131.
J. Medicinal Chemistry 26, 1986, pp. 1582–1589.

Primary Examiner—Cecilia Shen
Attorney, Agent, or Firm—Sprung, Horn, Kramer & Woods

[57] ABSTRACT

Benzopyran derivatives of the general formula I

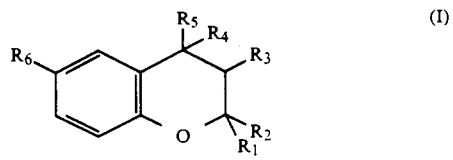

are disclosed. The compounds are therapeutic active compounds.

7 Claims, No Drawings

BENZOPYRAN DERIVATIVES, PROCESSES FOR THEIR PREPARATION AND THEIR USE AND PREPARATIONS CONTAINING THE COMPOUNDS

The invention relates to novel substituted benzopyran derivatives of the general formula I

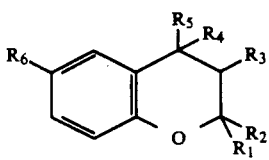

in which $R_1$ and $R_2$, which may be identical or different, denote hydrogen, $C_{1-6}$-alkyl, $C_{3-6}$-branched alkyl, $C_{3-7}$-cycloalkyl or, together with the carbon atom enclosed by them, denote $C_{3-7}$-spiroalkyl, $R_3$ denotes hydroxyl, $C_{1-8}$-alkoxy, formyloxy, $C_{1-8}$-alkylcarbonyloxy, $C_{1-8}$-alkoxycarbonyloxy, $C_{1-8}$-monoalkylaminocarbonyloxy or $C_{1-8}$-dialkylaminocarbonyloxy, where the $C_{1-8}$-alkyl or alkoxy groups may both be linear or branched, and $R_4$ stands for hydrogen or $R_3$ and $R_4$ together form a bond, $R_5$ denotes a heterocycle of the formula A

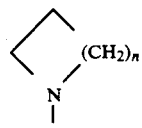

where n stands for 1, 2, 3 or 4, or a heterocycle of the formula B

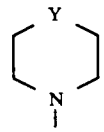

where Y stands for oxygen, sulphur, unsubstituted amino —NH—, substituted amino —NR$_7$— and R$_7$ denotes straight-chain $C_{1-9}$-alkyl, branched $C_{3-7}$alkyl, $C_{3-7}$-cycloalkyl, straight-chain or branched $C_{1-9}$-alkyl substituted by $C_{3-7}$-cycloalkyl, $C_{1-8}$-alkylcarbonyl, $C_{1-8}$-alkoxycarbonyl, benzyl, triphenylmethyl, phenyl, benzyloxycarbonyl, phenylcarbonyl or benzylcarbonyl or R$_5$ denotes a heterocycle of the formula C

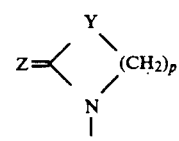

where X stands for oxygen or sulphur and n stands for 1, 2, 3 or 4, or a heterocycle of the formula D

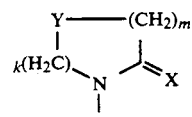

where m denotes 0, 1 or 2 and k denotes 1, 2 or 3, but in such a way that (m+k) is 1, 2 or 3 and furthermore X and Y have the meaning indicated for the formulae B and C, or a heterocycle of the formula E where Z stands for cyanimino N—CN, cis or trans nitromethylidene (c/t) CH—NO$_2$ or nitroimino N—NO$_2$, Y has the abovementioned meaning and p denotes 2 or 3, and R$_6$, depending on R$_5$, stands for the two classes of substituents R$_6$' and R$_6$", where, if R$_5$ denotes a heterocycle A, B, C or D, R$_6$ stands for the substituent class R$_6$' and R$_6$' denotes difluoromethoxy, trifluoromethoxy, trifluoroethoxy, tetrafluoroethoxy, difluoromethylthio, difluoromethylsulphinyl, difluoromethylsulphonyl, trifluoromethylthio, trifluoromethylsulphinyl, trifluoromethylsulphonyl, trifluoroethylthio, trifluoroethylsulphinyl or trifluoroethylsulphonyl, or, if R$_5$ denotes the heterocycle E, R$_6$ stands for the preceding substituent class R$_6$' and for the substituent class R$_6$" and R$_6$" denotes cyano, nitro, $C_{1-6}$-alkyl, $C_{3-8}$-cycloalkyl, formyl and $C_{1-6}$-alkylcarbonyl, where the heterocycle R$_5$ is in the trans position to the radical R$_3$ if R$_3$ and R$_4$ do not together denote a bond, but R$_4$ stands for hydrogen, and their salts and acid addition salts, tautomers and optical isomers, processes for their preparation, their use and preparations which contain these compounds.

For the sake of simplicity, the compounds according to the invention are defined in only one tautomeric form represented by formula I. However, the invention extends to all tautomeric forms of the compounds.

Although pharmaceutically tolerable salts and acid addition salts of the novel compounds of the formulae I and their tautomeric forms are preferred, all salts are within the field of the invention. All salts are useful for the preparation of compounds, even if the specific salt is only desired as an intermediate, such as, for example, if the salt is formed only for the purposes of purification or identification, or if it is used in the preparation of a pharmaceutically tolerable salt, for example by an ion exchange procedure.

Compounds of the general formula I and their salts and acid addition salts contain asymmetric carbon and sulphur atoms. The invention therefore also relates to the various optical isomers and diastereomers. The racemates can be separated into their optical antipodes by methods which are known per se.

The invention also relates to the novel compounds of the formulae IIa, IIIa and Va

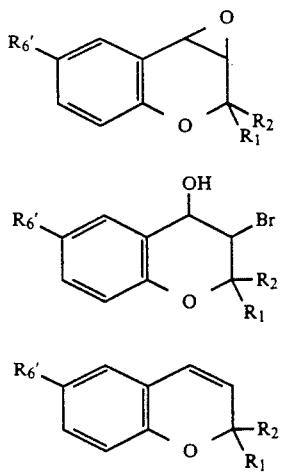

having the meanings indicated previously for $R_1$, $R_2$ and $R_6'$, and to the processes for their preparation. They are used as precursors or intermediates for the preparation of the final products according to the invention.

Compounds structurally related to the compounds of the present invention are described in U.S. Pat. No. 4,251,537, European Patent Specifications EP 0,076,075, EP 0,107,423 and in the Journal of Medicinal Chemistry 26, 1582 (1983), 27, 1127 (1984) and 29, 2194 (1986). However, the compounds of the present invention are neither specifically disclosed nor made obvious.

The compounds of the formula I according to the invention are distinguished in particular by a considerably higher intensity of action combined with a considerably prolonged duration of action compared to the known compounds.

If not stated otherwise, the alkyl groups and alkyl moieties or alkylene moieties of groups according to the invention may be straight-chain or branched and in each case preferably have 1 to 6 carbon atoms, preferably 1 to 4 carbon atoms, in particular 1 or 2 carbon atoms. The branched alkyl groups have at least 3 carbon atoms. Preferred alkyl or alkylene moieties are methyl, ethyl, n-propyl, isopropyl, or butyl and correspondingly methylene, ethylene, n- or iso-propylene and butylene.

Preferably, cycloalkyl groups and cycloalkyl moieties according to the invention such as cycloalkyl radicals of cycloalkylalkyl groups have 3 to 7 carbon atoms, in particular 3 to 6 carbon atoms. Cyclopropyl and cyclohexyl are particularly preferred.

Formyl is HCO—, formyloxy is HCOO—, $C_{1-8}$-alkylcarbonyloxy is $C_{1-8}$-alkyl-CO—O—, $C_{1-8}$-alkoxycarbonyloxy is $C_{1-8}$-alkyl-O—CO—O—, $C_{1-8}$-monoalkylaminocarbonyloxy is $C_{1-8}$-alkyl-NH-CO—O—, $C_{1-8}$-dialkylaminocarbonyloxy is ($C_{1-8}$-alkyl)$_2$-N—CO—O—. $C_{1-8}$-Alkylcarbonyl is $C_{1-8}$-alkyl-CO—, $C_{1-6}$-alkylcarbonyl is $C_{1-6}$-alkyl-CO—, $C_{1-8}$-alkoxycarbonyl is $C_{1-8}$-alkoxy-CO—.

The trifluoroethyl group or trifluoroethyl as a part of other radicals according to the invention such as trifluoroethoxy is preferably 2,2,2-trifluoroethyl.

The tetrafluoroethyl group or tetrafluoroethyl as a part of other radicals according to the invention such as tetrafluoroethoxy is preferably 2,2',1,1'-tetrafluoroethyl.

$C_{3-7}$-Cycloalkyl-substituted $C_{1-9}$-alkyl is preferably cyclopropylmethyl.

$R_1$ is preferably hydrogen, methyl or ethyl, of these particularly preferably methyl.

$R_2$ is preferably hydrogen, methyl or ethyl, of these particularly preferably methyl.

$R_1$ and $R_2$ together are particularly preferably both methyl.

If $R_1$ and $R_2$ preferably stands for branched alkyl or cycloalkyl, isopropyl or cyclopropyl are particularly preferred.

If $R_1$ and $R_2$ together with the carbon atom enclosed by them form a spiroalkyl ring, spirocyclopentyl and spirocyclohexyl are preferred.

$R_3$ preferably stands for hydroxyl or particularly preferably forms a bond together with $R_4$, so that a double bond exists between the $C_3$ and $C_4$ position of the benzopyran structure. The compounds according to the invention with this $C_3$=$C_4$ double bond are particularly preferred.

$R_7$ is preferably $C_{3-7}$-cycloalkyl-substituted straight-chain or branched $C_{1-9}$-alkyl.

If $R_3$ stands for alkoxy, ethoxy and particularly methoxy are preferred.

If $R_3$ stands for alkylcarbonyloxy, propionyloxy and particularly acetoxy and formyloxy are preferred.

$R_5$ is preferably a heterocycle of the formula A, C, D and E, of these in particular C, D and E, with the abovementioned meanings in each case for n, Y, X, m, k, p and Z, are preferred.

Of these, particularly preferred compounds are those in which:

C stands for 2-oxopyrrolidinyl and in particular 2-oxopiperidinyl,

D stands for 2-oxo-3-oxazolidinyl, 2-oxomorpholinyl and in particular 2-oxopiperazinyl and 2-oxohexahydropyrimidinyl, where the nitrogen atom standing for Y can be both unsubstituted and substituted by $R_7$ in the abovementioned meaning, where of all radicals of the formula D, unsubstituted 2-oxopiperazinyl or 2-oxopiperazinyl substituted by $R_7$ in the abovementioned meaning is most preferred, and E stands for 2-cyaniminoimidazolyl, where the nitrogen atom standing for Y can be both unsubstituted and substituted with $R_7$ in the abovementioned manner, or E stands in particular for 2-cyaniminothiazolyl.

If $R_6$ has the meaning $R_6'$, difluoromethoxy, trifluoromethoxy, trifluoromethylthio, difluoromethylthio, difluoromethylsulphonyl, trifluoromethylsulphonyl, trifluoroethoxy and tetrafluoroethoxy are preferred, of these difluoromethoxy, trifluoromethoxy, trifluoromethylthio, difluoromethylthio, difluoromethylsulphonyl, trifluoromethylsulphonyl, are particularly preferred, in particular trifluoromethoxy, trifluoromethylthio, difluoromethylsulphonyl, trifluoromethylsulphonyl, difluoromethylthio.

If $R_6$ has the meaning $R_6''$, cyano, $C_{1-6}$-alkyl, acetyl, $C_{3-6}$-cycloalkyl are preferred, of these cyano, methyl, ethyl, propyl and iso-propyl, cyclopropyl and acetyl are particularly preferred.

Particularly preferred compounds are those of the formulae Ia, Ia', Ib, Ib', Ic and Ic':

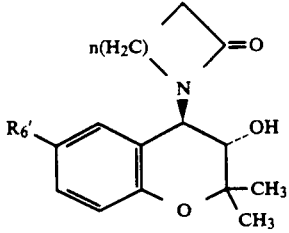

(Ia)

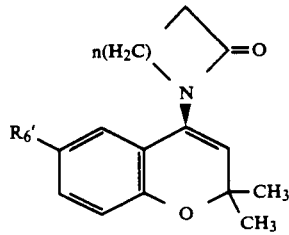

(Ia')

in which n denotes the number 2 or 3 and R6' denotes difluoromethoxy, trifluoromethoxy, trifluoromethylthio, difluoromethylthio, trifluoromethylsulphonyl, difluoromethylsulphonyl, trifluoroethoxy and tetrafluoroethoxy,

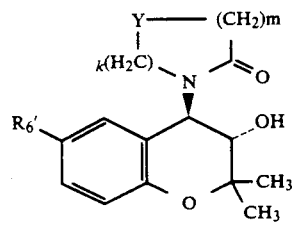

(Ib)

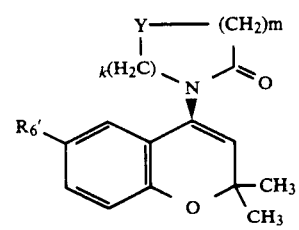

(Ib')

in which m denotes 0 or 1, k denotes 2, Y denotes O, NH, NR7 and R6' denotes difluoromethoxy, trifluoromethoxy, trifluoromethylthio, difluoromethylthio,trifluoromethylsulphonyl, difluoromethylsulphonyl, trifluoroethoxy and tetrafluoroethoxy,

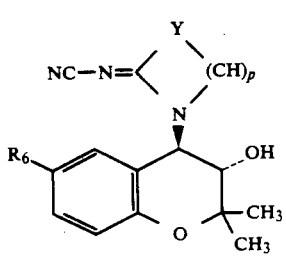

(Ic)

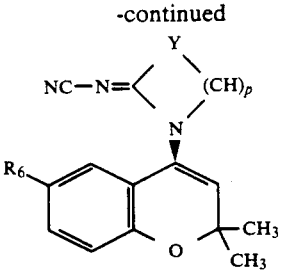

(Ic')

in which p denotes 2, Y denotes NH, NR7, S and R6 denotes difluoromethoxy, trifluoromethoxy, trifluoromethylthio, difluoromethylthio, trifluoromethylsulphonyl, difluoromethylsulphonyl, trifluoroethoxy and tetrafluoroethoxy, cyano, $C_{1-6}$-alkyl, acetyl and $C_{3-8}$-cycloalkyl.

The following compounds according to the invention, their salts and acid addition salts, tautomers and optical isomers are preferred:

1. 6-Difluoromethylthio-3,4-dihydro-2,2-dimethyl-trans-4-(2-oxo-1-pyrrolidinyl)-2H-benzo[b]pyran-3-ol
2. 6-Difluoromethylsulphinyl-3,4-dihydro-2,2-dimethyltrans -4-(2-oxo-1-pyrrolidinyl)-2H-benzo[b]pyran-3ol trans-4-(2-oxo-1-pyrrolidinyl)-2H-benzo[b]pyran-3-ol
3. 6-Difluoromethylsulphonly-3,4dihydro-2,2-dimethyl-trans -4-(2-oxo-1-pyrrolidinyl)-2H-benzo[b]pyran-3-ol
4. 6-Trifluoromethylthio-3,4-dihydro-2,2-dimethyltrans -4-(2-oxo-1-pyrrolidinyl)-2H-benzo[b]pyran-3-ol
5. 6-Trifluoromethylsulphinyl-3,4-dihydro-2,2-dimethyltrans -4-(2-oxo-1-pyrrolidinyl)-2H-benzo[b]pyran-3-ol
6. 6-Trifluoromethylsulphonyl-3,4-dihydro-2,2-dimethyltrans -4-(2-oxo-1-pyrrolidinyl)-2H-benzo[b]pyran-3-ol
7. 6-(2,2,2-Trifluoroethylthio)-3,4-dihydro-2,2-dimethyl -trans-4-(2-oxo-1-pyrrolidinyl)-2H-benzo[b]pyran-3-ol
8. 6-(2,2,2-Trifluoroethylsulphinyl)-3,4-dihydro-2,2-dimethyl -trans-4-(2-oxo-1-pyrrolidinyl)-2H-benzo[b]pyran-3-ol
9. 6-(2,2,2-Trifluoroethylsulphonyl)-3,4-dihydro-2,2-dimethyl -trans-4-(2-oxo-1-pyrrolidinyl)-2H-benzo[b]pyran-3-ol
10. 6-Difluoromethoxy-3,4-dihydro-2,2-dimethyl-trans-4(2-oxo-1-pyrrolidinyl) -2H-benzo[b]pyran-3-ol
11. 6-Trifluoromethoxy-3,4-dihydro-2,2-dimethyl-trans-4-(2-oxo-1-pyrrolidinyl)-2H-benzo[b]pyran-3-ol
12. 6-(2,2,2-Trifluoroethoxy)-3,4-dihydro-2,2-dimethyltrans -4-(2-oxo-1-pyrrolidinyl)-2H-benzo[b]pyran-3ol
13. 6-(1,1,2,2-Tetrafluoroethoxy)-3,4-dihydro-2,2-dimethyl -trans-4-(2-oxo-1-pyrrolidinyl)-2H-benzo[b]pyran-3-ol
14. 6-Difluoromethylthio-3,4-dihydro-2,2-dimethyl-trans-4-(2-oxo-1-piperidinyl)-2H-benzo[b]pyran-3-ol
15. 6-Difluoromethylsulphinyl-3,4-dihydro-2,2-dimethyltrans -4-(2-oxo-1-piperidinyl)-2H-benzo[b]pyran-3-ol
16. 6-Difluoromethylsulphonyl-3,4-dihydro-2,2-dimethyltrans -4-(2-oxo-1-piperidinyl)-2H-benzo[b]pyran-3-ol
17. 6-Trifluoromethylthio-3,4-dihydro-2,2-dimethyl-trans-4-(2-oxo-1-piperidinyl)-2H-benzo[b]pyran-3-ol 18. 6-Trifluoromethylsulphinyl-3,4-dihydro-2,2-dimethyltrans-4-(2-oxo-1-piperidinyl)-2H-benzo[b]pyran-3-ol
19. 6-Trifluoromethylsulphonyl-3,4-dihydro-2,2-dimethyltrans-4-(2-oxo-1-piperidinyl)-2H-benzo[b]pyran-3-ol
3,4-dihydro-2,2-di
20. 6-(2,2,2-Trifluoroethylthio)-methyl-trans-4-(2-oxo-1-piperidinyl)-2H-benzo[b]pyran-3-ol
21. 6-(2,2,2-Trifluoroethylsulphinyl)-3,4-dihydro-2,2-dimethyl-trans-4-(2-oxo-1-piperidinyl)-2H-benzo[b]pyran-3-ol
22. 6-(2,2,2-Trifluoroethylsulphonyl)-3,4-dihydro-2,2-dimethyl-trans-4-(2-oxo-1-piperidinyl)-2H-benzo[b]pyran-3-ol
23. 6-Difluoromethoxy-3,4-dihydro-2,2-dimethyl-trans-4(2-oxo-1-piperidinyl)-2H-benzo[b]pyran-3-ol
24. 6-Trifluoromethoxy-3,4-dihydro-2,2-dimethyltrans4-(2-oxo-1-piperidinyl)-2H-benzo[b]pyran-3-ol
25. 6-(2,2,2-Trifluoroethoxy)-3,4-dihydro-2,2-dimethyl-trans-4-(2-oxo-1-piperidinyl)-2H-benzo[b]pyran-3-ol
26. 6-(1,1,2,2-Tetrafluoroethoxy)-3,4-dihydro-2,2-dimethyl-trans-4-(2-oxo-1-piperidinyl)-2H-benzo[b]pyran-3-ol
27. 6-Difluoromethylthio-2,2-dimethyl-4-(2-oxo-1-pyrrolidinyl)-2H-benzo[b]pyran
28. 6-Difluoromethylsulphinyl-2,2-dimethyl-4-(2-oxo-1-pyrrolidinyl)-2H-benzo[b]pyran
29. 6-Difluoromethylsulphonyl-2,2-dimethyl-4-(2-oxo-1-pyrrolidinyl)-2H-benzo[b]pyran
30. 6-Trifluoromethylthio-2,2-dimethyl-4-(2-oxo-1-pyrrolidinyl)-2H-benzo[b]pyran
31. 6-Trifluoromethylsulphinyl-2,2-dimethyl-4-(2-oxo-1-pyrrolidinyl)-2H-benzo[b]pyran
32. 6-Trifluoromethylsulphonyl-2,2-dimethyl-4-(2-oxo-1-pyrrolidinyl)-2H-benzo[b]pyran
33. 6-(2,2,2-Trifluoroethylthio)-2,2-dimethyl-4-(2-oxo-1-pyrrolidinyl)-2H-benzo[b]pyran
34. 6-(2,2,2-Trifluoroethylsulphinyl)-2,2-dimethyl-4-(2-oxo-1-pyrrolidinyl)-2H-benzo[b]pyran
35. 6-(2,2,2-Trifluoroethylsulphonyl)-2,2-dimethyl-4-(2-oxo- 1-pyrrolidinyl)-2H-benzo[b]pyran
36. 6-Difluoromethoxy-2,2-dimethyl-4-(2-oxo-1-pyrrolidinyl)-2H-benzo[b]pyran
37. 6-Trifluoromethoxy-2,2-dimethyl-4-(2-oxo-1-pyrrolidinyl)-2H-benzo[b]pyran 38. 6-(2,2,2-Trifluoroethoxy)-2,2-dimethyl-4-(2-oxo-1-pyrrolidinyl)-2H-benzo[b]pyran
39. 6-(1,1,2,2-Tetrafluoroethoxy)-2,2-dimethyl-4-(2-oxo1-pyrrolidinyl)-2H-benzo[b]pyran
40. 6-Difluoromethylthio-2,2-dimethyl-4-(2-oxo-1-piperidinyl)-2H-benzo[b]pyran
41. 6-Difluoromethylsulphinyl-2,2-dimethyl-4-(2-oxo-1-piperidinyl)-2H-benzo[b]pyran
42. 6-Difluoromethylsulphonyl-2,2-dimethyl-4-(2-oxo-1-piperidinyl)-2H-benzo[b]pyran
43. 6-Trifluoromethylthio-2,2-dimethyl-4-(2-oxo-1-piperidinyl)-2H-benzo[b]pyran
44. 6-Trifluoromethylsulphinyl-2,2-dimethyl-4-(2-oxo-1-piperidinyl)-2H-benzo[b]pyran
45. 6-Trifluoromethylsulphonyl-2,2-dimethyl-4-(2-oxo-1-piperidinyl)-2H-benzo[b]pyran
46. 6-(2,2,2-Trifluoroethylthio)-2,2-dimethyl-4-(2-oxo1-piperidinyl)-2H-benzo[b]pyran
47. 6-(2,2,2-Trifluoroethylsulphinyl)-2,2-dimethyl-4-(2-oxo-1-piperidinyl)-2H-benzo[b]pyran
48. 6-(2,2,2-Trifluoroethylsulphonyl)-2,2-dimethyl-4-(2-oxo-1-piperidinyl)-2H-benzo[b]pyran
49. 6-Difluoromethoxy-2,2-dimethyl-4-(2-oxo-1-piperidinyl)-2H-benzo[b]pyran
50. 6-Trifluoromethoxy-2,2-dimethyl-4-(2-oxo-1-piperidinyl)-2H-benzo[b]pyran
51. 6-(2,2,2-Trifluoroethoxy)-2,2-dimethyl-4-(2-oxo-1-/-/ piperidinyl)-2H-benzo[b]pyran
52. 6-(1,1,2,2-Tetrafluoroethyoxy)-2,2-dimethyl-4-(2-oxo-1-piperidinyl)-2H-benzo[b]pyran
53. 6-Cyano-3,4-dihydro-2,2-dimethyl-trans-4-(2-cyanimino-3-imidazolidin-1-yl)-2H-benzo[b]pyran-3-ol
54. 6-Difluoromethylthio-3,4-dihydro-2,2-dimethyl-trans4-(2-cyanimino-3-imidazolidin-1-yl)-2H-benzo[b]pyran-3-ol
55. 6-Difluoromethylsulphinyl-3,4-dihydro-2,2-dimethyltrans -4-(2-cyanimino-3-imidazolidin-1-yl)-2H-benzo[b]pyran-3-ol
56. 6-Difluoromethylsulphonyl-3,4-dihydro-2,2-dimethyltrans-4-(2-cyanimino-3-imidazolidin-1-yl)-2H-benzo[b]pyran-3-ol
57. 6-Trifluoromethylthio-3,4-dihydro-2,2-dimethyl-trans-4-(2-cyanimino-3-imidazolidin-1-yl)-2H-benzo[b]pyran-3-ol
58. 6-Trifluoromethylsulphinyl-3,4-dihydro-2,2-dimethyltrans-4-(2-cyanimino-3-imidazolidin-1-yl)-2H-benzo[b]pyran-3-ol
59. 6-Trifluoromethylsulphonyl-3,4-dihydro-2,2-dimethyltrans-4-(2-cyanimino-3-imidazolidin-1-yl)-2H-benzo[b]pyran-3-ol
60. 6-Difluoromethoxy-3,4-dihydro-2,2-dimethyl-trans-4-(2-cyanimino-3-imidazolidin-1-yl)-2H-benzo[b]pyran3-ol
61. 6-Trifluoromethoxy-3,4-dihydro-2,2-dimethyltrans4-(2-cyanimino-3-imidazolidin-1-yl)-2H-benzo[b]pyran-3-ol
62. 6-Cyano-2,2-dimethyl-4-(2-cyanimino-3-imidazolidin-1-yl)-2H-benzo[b]pyran
63. 6-Difluoromethylthio-2,2-dimethyl-4-(2-cyanimino-3-imidazolidin-1-yl)-2H-benzo[b]pyran
64. 6-Difluoromethylsulphinyl-2,2-dimethyl-4-(2-cyanimino-3-imidazolidin-1yl)-2H-benzo[b]pyran
65. 6-Difluoromethylsulphonyl-2,2-dimethyl-4-(2-cyanimino-3-imidazolidin-1-yl) -2H-benzo[b]pyran
66. 6-Trifluoromethylthio-2,2-dimethyl-4-(2-cyanimino-3-imidazolidin-1-yl)-2H-benzo[b]pyran
67. 6-Trifluoromethylsulphinyl-2,2-dimethyl-4-(2-cyanimino-3-imidazolidin-1-yl)-2H-benzo[b]pyran
68. 6-Trifluoromethylsulphonyl-2,2-dimethyl-4-(2-cyanimino-3-imidazolidin-1-yl)-2H-benzo[b]pyran
69. 6-Difluoromethoxy-2,2-dimethyl-4-(2-cyanimino-3-imidazolidin-1-yl)-2H-benzo[b]pyran
70. 6-Trifluoromethoxy-2,2-dimethyl-4-(2-cyanimino-3-imidazolidin-1-yl) -2H-benzo[b]pyran
71. 6-Trifluoromethoxy-2,2-dimethyl-4-(2-oxo-4-N-cyclopropylmethyl-piperazin-1-yl)-2H-benzo[b]pyran
72. 6-Difluoromethylthio-3,4-dihydro-2,2-dimethyltrans-4-(2-oxo-4-N-methylpiperazin-1-yl)-2H-benzo[b]pyran3-ol
73. 6-Difluoromethylsulphinyl-3,4-dihydro-2,2-dimethyltrans-4-(2-oxo-4-N-methylpiperazin-1-yl)-2H-benzo [b]pyran-3-ol
74. 6-Difluoromethylsulphonyl-3,4-dihydro-2,2-dimethyltrans-4-(2-oxo-4-N-methylpiperazin-1-yl)-2H-benzo[b]pyran-3-ol 75. 6-Trifluoromethylthio-3,4-dihydro-2,2-dimethyl-trans-4-(2-oxo-4-N-methylpiperazin-1-yl)-2H-benzo[b]pyran-3-ol
76. 6-Trifluoromethylsulphinyl-3,4-dihydro-2,2-dimethyltrans-4-(2-oxo-4-N-methylpiperazin-1-yl)-2H-benzo[b]pyran-3-ol
77. 6-Trifluoromethylsulphonyl-3,4-dihydro-2,2-dimethyltrans-4-(2-oxo-4-N-methylpiperazin-1-yl)-2H-benzo[b]pyran-3-ol
78. 6-Difluoromethoxy-3,4-dihydro-2,2-d (2-oxo-4-N-methylpiperazin-1-yl)-2H-benzo[b]pyran3-ol
79. 6-Trifluoromethoxy-3,4-dihydro-2,2-dimethyl-trans-4-(2-oxo-4-N-methylpiperazin-1-yl)-2H-benzo[b]pyran3-ol
80. 6-Trifluoromethoxy-2,2-dimethyl-4-(2-oxo-4-N-isopropylpiperazin-1-yl)-2H-benzo[b]pyran
81. 6-Difluoromethylthio-2,2-dimethyl-4-(2-oxo-4-N-methylpiperazin-1-yl)-2H-benzo[b]pyran
82. 6-Difluoromethylsulphinyl-2,2-dimethyl-4-(2-oxo-4-N-methylpiperazin-1-yl) -2H-benzo[b]pyran
83. 6-Difluoromethylsulphonyl-2,2-dimethyl-4-(2-oxo-4-N-methylpiperazin-1-yl)-2H-benzo[b]pyran
84. 6-Trifluoromethylthio-2,2-dimethyl-4-(2-oxo-4-N-methylpiperazin-1-yl)-2H-benzo[b]pyran
85. 6-Trifluoromethylsulphinyl-2,2-dimethyl-4-(2-oxo-4-N-methylpiperazin-1-yl)-2H-benzo[b]pyran
86. 6-Trifluoromethylsulphonyl-2,2-dimethyl-4-(2-oxo-4-N-methylpiperazin-1-yl)-2H-benzo[b]pyran
87. 6-Difluoromethoxy-2,2-dimethyl-4-(2-oxo-4-N-methyl-piperazin-1-yl) -2H-benzo[b]pyran
88. 6-Trifluoromethoxy-2,2-dimethyl-4-(2-oxo-4-N-methylpiperazin-1-yl)-2H-benzo[b]pyran
89. 6-Cyano-3,4-dihydro-2,2-dimethyl-trans-4-(2-cyanimino-3-thiazolidin-1-yl)-2H-benzo[b]pyran-3-ol
90. 6-Difluoromethylthio-3,4-dihydro-2,2-dimethyl-trans-4-(2-cyanimino-3-thiazolidin-1-yl)-2H-benzo[b]pyran-3-ol
91. 6-Difluoromethylsulphinyl-3,4-dihydro-2,2-dimethyltrans-4-(2-cyanimino-3-thiazolidin-1-yl)-2H-benzo[b]pyran-3-ol
92. 6-Difluoromethylsulphonyl-3,4-dihydro-2,2-dimethyltrans-4-(2-cyanimino-3-thiazolidin-1-yl)-2H-benzo[b]pyran-3-ol
93. 6-Trifluoromethylthio-3,4-dihydro-2,2-dimethyl-trans-4-(2-cyanimino-3-thiazolidin-1-yl)-2H-benzo[b]pyran-3-ol
94. 6-Trifluoromethylsulphinyl-3,4-dihydro-2,2-dimethyltrans-4-(2-cyanimino-3-thiazolidin-1-yl)-2H-benzo[b]pyran-3-ol
95. 6-Trifluoromethylsulphonyl-3,4-dihydro-2,2-dimethyltrans-4-(2-cyanimino-3-thiazolidin-1-yl)-2H-benzo[b]pyran-3-ol
96. 6-Difluoromethoxy-3,4-dihydro-2,2-dimethyl-trans-4-(2-cyanimino-3-thiazolidin-1-yl) -2H-benzo[b]pyran-3-ol
97. 6-Trifluoromethoxy-3,4-dihydro-2,2-dimethyltrans-4-(2-cyanimino-3-thiazolidin-1-yl)-2H-benzo[b]pyran-3-ol
98. 6-Cyano-2,2-dimethyl-4-(2-cyanimino-3-thiazolidin-1-yl) -2H-benzo[b]pyran
99. 6-Difluoromethylthio-2,2-dimethyl-4-(2-cyanimino-3-thiazolidin-1-yl) -2H-benzo[b]pyran
100. 6-Difluoromethylsulphinyl-2,2-dimethyl-4-(2-cyanimino-3-thiazolidin-1-yl)-2H-benzo[b]pyran
101. 6-Difluoromethylsulphonyl-2,2-dimethyl-4-(2-cyanimino 3-thiazolidin-1-yl)-2H-benzo[b]pyran
102. 6-Trifluoromethylthio-2,2-dimethyl-4-(2-cyanimino-3-thiazolidin-1-yl) -2H-benzo[b]pyran
103. 6-Trifluoromethylsulphinyl-2,2-dimethyl-4-(2-cyanimino-3-thiazolidin-1-yl)-2H-benzo[b]pyran
104. 6-Trifluoromethylsulphonyl-2,2-dimethyl-4-(2-cyanimino -3-thiazolidin-1-yl)-2H-benzo[b]pyran
105. 6-Difluoromethoxy-2,2-dimethyl-4-(2-cyanoimino-3-thiazolidin -1-yl)-2H-benzo[b]pyran
106. 6-Trifluoromethoxy-2,2-dimethyl-4-(2-cyanimino-thiazolidin-1-yl)-2H-benzo[b]pyran
107. 6-Cyano-3,4-dihydro-2,2-dimethyl-trans-4-(2-cyanimino-3-N-methylimidazolidin-1-yl)-2H-benzo[b]pyran-3-ol
108. 6-Difluoromethylthio-3,4-dihydro-2,2-dimethyl-trans-4-(2-cyanimino-3-N-methylimidazolidin-1-yl)-2H-benzo[b]pyran-3-ol
109 6-Difluoromethylsulphinyl-3,4-dihydro-2,2-dimethyltrans-4-(2-cyanimino-3-N-methylimidazolidin-1-yl)2H-benzo[b]pyran-3-ol
110. 6-Difluoromethylsulphonyl-3,4-dihydro-2,2-dimethyltrans-4-(2-cyanimino-3-N-methylimidazolidin-1-yl)2H-benzo[b]pyran-3-ol
111. 6-Trifluoromethylthio-3,4-dihydro-2,2-dimethyl-trans-4-(2-cyanimino-3-N-methylimidazolidin-1-yl)2H-benzo[b]pyran-3-ol
112. 6-Trifluoromethylsulphinyl-3,4-dihydro-2,2-dimethyltrans-4-(2-cyanimino-3-N-methylimidazolidin-1-yl)-2H-benzo[b]pyran-3-ol
113. 6-Trifluoromethylsulphonyl-3,4-dihydro-2,2-dimethyltrans-4-(2-cyanimino-3-N-methylimidazolidin-1-yl)2H-benzo[b]pyran-3-ol
114. 6-Difluoromethoxy-3,4-dihydro-2,2-dimethyl-trans-4(2-cyanimino-3-N-methylimidazolidin-1-yl)-2H-benzo[b]pyran-3-ol
115. 6-Trifluoromethoxy-3,4-dihydro-2,2-dimethyl-trans4-(2-cyanimino-3-N-methylimidazolidin-1-yl)-2H-benzo[b]pyran-3-ol
116. 6-Cyano-2,2-dimethyl-4-(2-cyanimino-3-N-methylimidazolidin- 1-yl)-2H-benzo[b]pyran
117. 6-Difluoromethylthio-2,2-dimethyl-4-(2-cyanimino-3-N methylimidazolidin-1-yl)-2H-benzo[b]pyran
118. 6-Difluoromethylsulphinyl-2,2-dimethyl-4-(2-cyanimino-3-N-methylimidazolidin-1-yl)-2H-benzo[b]pyran
119. 6-Difluoromethylsulphonyl-2,2-dimethyl-4-(2-cyanimino-3-N-methylimidazolidin-1-yl)-2H-benzo[b]pyran
120. 6-Trifluoromethylthio-2,2-dimethy-4-(2-cyanimino-3-Nmethylimidazolidin-1-yl) -2H-benzo[b]pyran
121. 6-Trifluoromethylsulphinyl-2,2-dimethyl-4-(2-cyanimino-3-N-methylimidazolidin-1-yl)-2H-benzo[b]pyran
122. 6-Trifluoromethylsulphonyl-2,2-dimethyl-4-(2-cyanimino-3-N-methylimidazolidin-1-yl)-2H-benzo[b]pyran
123. 6-Difluoromethoxy-2,2-dimethyl-4-(2-cyanimino-3-N-methylimidazolidin-1-yl)-2H-benzo[b]pyran
124. 6-Trifluoromethoxy-2,2-dimethyl-4-(2-cyanimino-3-N-methylimidazolidin-1-yl)-2H-benzo[b]pyran
125. 6-Cyano-3,4-dihydro-2,2-dimethyl-trans-4-(2-cyanimino-3-hexahydropyrimidin-1-yl)-2H-benzo[b]pyran-3-ol
126. 6-Difluoromethylthio-3,4-dihydro-2,2-dimethyl-trans-4-(2-cyanimino-3-hexahydropyrimidin-1-yl)-2H-benzo[b]pyran-3-ol 127. 6-Difluoromethylsulphinyl-3,4-dihydro-2,2-dimethyltrans-4-(2-cyanimino-3-hexahydropyrimidin-1-yl)-2H-benzo[b]pyran-3-ol
128. 6-Difluoromethylsulphonyl-3,4-dihydro-2,2-dimethyltrans-4-(2-cyanimino-3-hexahydropyrimidin-1-yl)-2H-benzo[b]pyran-3-ol
129. 6-Trifluoromethylthio-3,4-dihydro-2,2-dimethyl-trans-4-(2-cyanimino-3-hexahydropyrimidin-1-yl)-2H-benzo[b]pyran-3-ol
130. 6-Trifluoromethylsulphinyl-3,4-dihydro-2,2-dimethyltrans-4-(2-cyanimino-3-hexahydropyrimidin-1-yl)-2H-benzo[b]pyran-3-ol
131. 6-Trifluoromethylsulphonyl-3,4-dihydro-2,2-dimethyltrans-4-(2-cyanimino-3-hexahydropyrimidin-1-yl)-2H-benzo[b]pyran-3-ol
132. 6-Difluoromethoxy-3,4-dihydro-2,2-dimethyl-trans-4 -(2-cyanimino-3-hexahydropyrimidin-1-yl)-2H-benzo[b]pyran-3-ol yl-trans
133. 6-Trifluoromethoxy-3,4-dihydro-2,2-dimethyl-trans-4-(2-cyanimino-3-hexahydropyrimidin-1-yl)-2H-benzo[b]pyran-3-ol
134. 6-Cyano-2,2-dimethyl-4-(2-cyanimino-3-hexahydropyrimidin-1yl) -2H-benzo[b]pyran
1345. 6-Difluoromethylthio-2,2-dimethyl-4-(2-cyanimino-3-hexahydropyrimidin-1-yl) -2H-benzo[b]pyran
136. 6-Difluoromethylsulphinyl-2,2-dimethyl-4-(2-cyanimino-3-hexahydropyrimidin-1yl) -2H-benzo[b]pyran
137. 6-Difluoromethylsulphonyl-2,2-dimethyl-4-(2-cyanimino-3-hexahydropyrimidin-1-yl) -2H-benzo[b]pyran
138. 6-Trifluoromethylthio-2,2l-dimethyl-4-(2-cyanimino-3-hexahydropyrimidin-1-yl) -2H-benzo[b]pyran
139. 6-Trifluoromethylsulphinyl-2,2-dimethyl-4-(2-cyanimino-3-hexahydropyrimidin-1-yl) -2H-benzo[b]pyran
140. 6-Trifluoromethylsulphonyl-2,2-dimethyl-4-(2-cyanimino-3-hexahydropyrimidin-1-yl) -2H-benzo[b]pyran
141. 6-Difluoromethoxy-2,2-dimethyl-4-(2-cyanimino-3-hexahydropyrimidin-1yl) -2H-benzo[b]pyran
142. 6-Trifluoromethoxy-2,2-dimethyl-4-(2-cyanimino-3-hexahydropyrimidin-1-yl) -2H-benzo[b]pyran
143. 6-Difluoromethylthio-3,4-dihydro-2,2-dimethyl-trans-4-(2-oxo-4-piperazin-1yl) -2H-benzo[b]pyran-3ol
144. 6-Difluoromethylsulphinyl-3,4-dihydro-2,2-dimethyltrans-4-(2-oxo-4-piperazin-1-yl) -2H-benzo[b]pyran-3-ol
145. 6-Difluoromethylsulphonyl-3,4-dihydro-2,2-dimethyltrans-4-(2-oxo-4-piperazin-1-yl) -2H-benzo[b]pyran-3-ol
146. 6-Trifluoromethylthio-3,4-dihydro-2,2-dimethyl-trans-4-(2-oxo-4-piperazin-1-yl) -2H-benzo[b]pyran-3-ol
147. 6-Trifluoromethylsulphinyl-3,4-dihydro-2,2-dimethyltrans-4-(2-oxo-4-piperazin-1-yl) -2H-benzo[b]pyran-3-ol
148. 6-Trifluoromethylsulphonyl-3,4-dihydro-2,2-dimethyltrans-4-(2-oxo-4-piperazin-1-yl) -2H-benzo[b]pyran-3-ol
149. 6-Difluoromethoxy-3,4-dihydro-2,2-dimethyl-trans-4(2-oxo-4-piperazin-1-yl)-2H-benzo[b]pyran-3-ol
150. 6-Trifluoromethoxy-3,4-dihydro-2,2-dimethyl-trans-4-(2-oxo-4-piperazin-1-yl)-2H-benzo[b]pyran-3-ol
151. 6-Difluoromethylthio-2,2-dimethyl-4-(2-oxo-4-piperazin-1-yl) -2H-benzo[b]pyran
152. 6-Difluoromethylsulphinyl-2,2-dimethyl-4-(2-oxo-4-piperazin-1-yl) -2H-benzo[b]pyran
153. 6-Difluoromethylsulphonyl-2,2-dimethyl-4-(2-oxo-4-piperazin-1-yl)-2H-benzo[b]pyran
154. 6-Trifluoromethylthio-2,2-dimethyl-4-(2-oxo-4-piperazin-1-yl)-2H-benzo[b]pyran
155. 6-Trifluoromethylsulphinyl-2,2-dimethyl-4-(2-oxo-4-piperazin-1-yl)-2H-benzo[b]pyran
156. 6-Trifluoromethylsulphonyl-2,2-dimethyl-4-(2-oxo-4-piperazin-1-yl)-2H-benzo[b]pyran
157. 6-Difluoromethoxy-2,2-dimethyl-4-(2-oxo-4-piperazin-1-yl) -2H-benzo[b]pyran
158. 6-Trifluoromethoxy-2,2-dimethyl-4-(2-oxo-4--piperazin-1-yl) -2H-benzo[b]pyran
159. 6-Difluoromethylthio-3,4-dihydro-2,2-dimethyl-trans-4-(2-oxo-4-N-benzylpiperazin-1-yl)-2H-benzo[b]pyran-3-ol
160. 6-Difluoromethylsulphinyl-3,4-dihydro-2,2-dimethyltrans -4-(2-oxo-4-N-benzylpiperazin-1-yl)-2H-benzo[b]pyran-3-ol
161. 6-Difluoromethylsulphonyl-3,4-dihydro-2,2-dimethyltrans-4-(2-oxo-4-N-benzylpiperazin-1-yl)-2H-benzo[b]pyran-3-ol
162. 6-Trifluoromethylthio-3,4-dihydro-2,2-dimethyl-trans-4-(2-oxo-4-N-benzylpiperazin-1-yl)-2H-benzo[b]pyran-3-ol
163. 6-Trifluoromethylsulphinyl-3,4-dihydro-2,2-dimethyltrans-4-(2-oxo-4-N-benzylpiperazin-1-yl)-2H-benzo[b]pyran-3-ol
164. 6-Trifluoromethylsulphonyl-3,4-dihydro-2,2-dimethyl-trans-4-(2-oxo-4-N-benzylpiperazin-1-yl)-2H-benzo[b]pyran-3-ol
165. 6-Difluoromethoxy-3,4-dihydro-2,2-dimethyl-trans-4(2-oxo-4-N-benzylpiperazin-1-yl)-2H-benzo[b]pyran-3-ol
166. 6-Trifluoromethoxy-3,4-dihydro-2,2-dimethyltrans -4-(2-oxo-4-N-benzylpiperazin-1-yl)-2H-benzo[b]pyran-3-ol
167. 6-Difluoromethylthio-2,2-dimethyl-4-(2-oxo-4-N-benzylpiperazin-1-yl) -2H-benzo[b]pyran
168. 6-Difluoromethylsulphinyl-2,2-dimethyl-4-(2-oxo-4-N-benzylpiperazin-1-yl) -2H-benzo[b]pyran
169 6-Difluoromethylsulphonyl-2,2-dimethyl-4-(2-oxo-4-N-benzylpiperazin-1-yl) -2H-benzo
170. 6-Trifluoromethylthio-2,2-dimethyl-4-(2-oxo-4-N-benzylpiperazin-1-yl) -2H-benzo[b]pyran
171. 6-Trifluoromethylsulphinyl-2,2-dimethyl-4-(2-oxo-4-N-benzylpiperazin-1-yl) -2H-benzo[b]pyran
172. 6-Trifluoromethylsulphonyl-2,2-dimethyl-4-(2-oxo-4-N-benzylpiperazin-1-yl) -2H-benzo[b]pyran
173. 6-Difluoromethoxy-2,2-dimethyl-4-(2-oxo-4--N-benzylpiperazin-1-yl) -2H-benzo[b]pyran
174. 6-Trifluoromethoxy-2,2-dimethyl-4-(2-oxo-4-N-benzyl-piperazin-1-yl)-2H-benzo[b]pyran
175. 6-Difluoromethylthio-3,4-dihydro-2,2-dimethyl-trans-4-(2-oxo-4-N-cyclopropylmethyl-piperazin-1-yl)-2H-benzo[b]pyran-3-ol
176. 6-Difluoromethylsulphinyl-3,4-dihydro-2,2-dimethyltrans-4-(2-oxo-4-N-cyclopropylmethyl-piperazin-1-yl)-2H-benzo[b]pyran-3-ol
177. 6-Difluoromethylsulphonyl-3,4-dihydro-2,2-dimethyltrans-4-(2-oxo-4-N-cyclopropylmethyl-piperazin-1-yl)-2H-benzo[b]pyran-3-ol 178. 6-Trifluoromethylthio-3,4-dihydro-2,2-dimethyl-trans-4-(2-oxo-4-N-cyclopropylmethyl-piperazin-1-yl)-2H-benzo[b]pyran-3-ol
179. 6-Trifluoromethylsulphinyl-3,4-dihydro-2,2-dimethyltrans-4-(2-oxo-4-N-cyclopropylmethyl-piperazin-1-yl)-2H-benzo[b]pyran-3-ol
180. 6-Trifluoromethylsulphonyl-3,4-dihydro-2,2-dimethyltrans-4-(2-oxo-4-N-cyclopropylmethyl-piperazin-12 yl)-2H-benzo[b]pyran-3-ol
181. 6-Difluoromethoxy-3,4-dihydro-2,2-dimethyl-trans-4-(2-oxo-4-N-cyclopropylmethyl-piperazin-1-yl)-2H-benzo[b]pyran-3-ol
182. 6-Trifluoromethoxy-3,4-dihydro-2,2-dimethyl-trans-4-(2-oxo-4-N-cyclopropylmethyl-piperazin-1-yl)-2H-benzo[b]pyran-3-ol
183. 6-Difluoromethylthio-3,4-dihydro-2-,2-dimethyl-trans4-(2-oxo-4-N-isopropylpiperazin-1-yl)-2H-benzo[b]pyran-3-ol
184. 6-Difluoromethylsulphinyl-3,4-dihydro-2,2-dimethyltrans-4-(2-oxo-4-N-isopropylpiperazin-1-yl)-2H-benzo[b]pyran-3-ol
185. 6-Difluoromethylsulphonyl-3,4-dihydro-2,2-dimethyltrans-4-(2-oxo-4-N-isopropylpiperazin-1-yl)-2H-benzo[b]pyran-3-ol
186. 6-Trifluoromethylthio-3,4-dihydro-2,2-dimethyl-trans-4-(2-oxo-4-N-isopropylpiperazin-1-yl)-2H-benzo[b]pyran-3-ol
187. 6-Trifluoromethylsulphinyl-3,4-dihydro-2,2-dimethyltrans-4-(2-oxo-4-N-isopropylpiperazin-1-yl)-2H-benzo[b]pyran-3-ol
188. 6-Trifluoromethylsulphonyl-3,4-dihydro-2,2-dimethyltrans-4-(2-oxo-4-N-isopropylpiperazin-1-yl)-2H-benzo[b]pyran-3-ol
189. 6-Difluoromethoxy-3,4-dihydro-2,2-dimethyl-trans-4-(2-oxo-4-N-isopropylpiperazin-1-yl)-2H-benzo[b]pyran-3-ol
190. 6-Trifluoromethoxy-3,4-dihydro-2,2-dimethyl-trans4-(2-oxo-4-N-isopropylpiperazin-1-yl)-2H-benzo[b]pyran-3-ol
191. 6-Difluoromethoxy-2,2-dimethyl-4-(2-oxo-4-N-isopropyl-piperazin-1-yl}-2H-benzo[b]pyran
192. 6-Difluoromethoxy-2,2-dimethyl-4-(2-oxo-4-N-cyclopropylmethyl-piperazin-1-yl) -2H-benzo[b]pyran
193. 6-Trifluoromethylthio-2,2-dimethyl-4(2-oxo-4-N-cyclopropylmethyl-piperazin-1-yl) -2H-benzo[b]pyran
194. 6-Difluoromethoxy-3,4-dihydro-2,2-dimethyl-trans-4-(1-pyrrolidinyl)-2H-benzo[b]pyran-3-ol
195 6-Difluoromethoxy-3,4-dihydro-2,2-dimethyl-trans-4(2-oxo-3-imidazolidin-1-yl)-2H-benzo[b]pyran-3-ol
196. 6-Trifluoromethoxy-3,4-dihydro-2,2-dimethyl-trans4-(2-oxo-4-N-methoxycarbonyl-piperazin-1-yl)-2H-benzo[b]pyran-3-ol
197. 6-Trifluoromethoxy-3,4-dihydro-2,2-dimethyl-trans-4-(2-oxo-4-N-acetyl-piperazin-1-yl)-2H-benzo[b]pyran-3-ol
198. 6-Trifluoromethylthio-3,4-dihydro-2,2-dimethyl-trans-4-(2-oxo-4-N-methoxycarbonyl-piperazin-1-yl)2H-benzo[b]pyran-3-ol
199. 6-Difluoromethoxy-3,4-dihydro-2,2-dimethyl-trans-4-(2-oxo-3-N-methylimidazolidin-1-yl)-2H-benzo[b]pyran-3-ol
200. 6-Difluoromethoxy-3,4-dihydro-2,2-dimethyl-trans-4-(2-oxo-3-oxazolidin-1-yl)-2H-benzo[b]pyran-3-ol
201. 6-Difluoromethoxy-3,4-dihydro-2,2-dimethyl-trans-4(1-piperidinyl)-2H-benzo[b]pyran-3-ol
202. 6-Difluoromethoxy-3,4-dihydro-2,2-dimethyl-trans-4(1-N-morpholinyl)-2H-benzo[b]pyran-3-ol
203. 6-Difluoromethoxy-3,4-dihydro-2,2-dimethyl-trans-4(2-oxo-3-N-phenylimidazolidin-1-yl)-2H-benzo[b]pyran-3-ol
204. 6-Difluoromethoxy-3,4-dihydro-2,2-dimethyl-trans-4(1-aza-2-oxo-1-cycloheptyl)-2H-benzo[b]pyran-3-ol
205. 6-Difluoromethoxy-3,4-dihydro-2,2-dimethyl-trans-4-(2-oxo-4-N-acetyl-piperazin-1-yl)-2H-benzo[b]pyran-3-ol
206. 6-Difluoromethoxy-2,2-dimethyl-4-(2-oxo-3-N-methylhexahydropyrimidin-1-yl)-2H-benzo[b]pyran .
207. 6-Difluoromethoxy-2,2-dimethyl-4-(2-oxo-3-thiazolidin-1-yl) -2H-benzo[b]pyran
208 6-Difluoromethoxy-3,4-dihydro-2,2-dimethyl-trans-4-(2-oxo-3-thiazolidin-1-yl)-2H-benzo[b]pyran-3-ol
209. 6-Cyano-3,4-dihydro-2,2-dimethyl-trans-4-(2-nitromethylidene-3-imidazolidin-1-yl)-2H-benzo[b]pyran-3-ol
210. 6-Trifluoromethylthio-3,4-dihydro-2,2-dimethyl-trans-4-(2-nitromethylidene-3-imidazolidin-1-yl)-2H-benzo[ b]pyran-3-ol
211. 6-Cyano-3,4-dihydro-2,2-dimethyl-trans-4-(2-nitroimino-3-imidazolidin-1-yl)-2H-benzo[b]pyran-3-ol
212. 6-Trifluoromethylthio-3,4-dihydro-2,2-dimethyl-trans-4-(2-nitroimino-3-imidazolidin-1-yl)-2H-benzo[b]pyran-3-ol The compounds 1–52 are particularly preferred, but in particular 1 to 6, 11, 14 to 19, 23, 24, 27 to 32, 37, 40 to 45, 50 and 4, 6, 17, 19, 23, 30, 32, 43, 45 and 50 are very particularly preferred.

The compounds of the formula I according to the invention, their physiologically tolerable salts and acid addition salts and their tautomers and optical isomers are therapeutic active compounds, have superior pharmacological action and are useful medicaments. In particular, they show vasodilating and vascular spasmolytic, in particular broncholytic action, it being possible for the vascular spasmolytic action to develop in the entire vascular system or else more or less isolated in prescribed vascular areas such as cerebral, coronary or peripheral vessels.

The compounds according to the invention in particular have hypotensive action and can thus be used as antihypertensive agents.

The substances according to the invention are distinguished by a considerable lowering of the arterial blood pressure. Doses of 0.01–10 mg/kg s.c. led to a lowering of the blood pressure by at least 20 % in hypertensive rats.

The substances according to the invention are distinguished by a particular influence on the potassium ion circulation in the cells. In particular, they are potassium channel activators. They are suitable for the prophylaxis and for the treatment of the following disorders in mammals, in particular the human:
1. high blood pressure, in particular high arterial blood pressure,
2. cardiac insufficiency, coronary insufficiency, angina pectoris,
3. obstructive arterial disease and peripheral circulatory disturbances,
4. cerebral insufficiency, migraine, vertigo, disorders of the inner ear or the hearing apparatus,
5. elevated internal ocular pressure, glaucoma, weakness of vision, 6. renal insufficiency, organic disorders of the efferent urinary passages and the accessory glands of the urinary passages, potency disturbances,
7. organic disturbances of the gastrointestinal tract and also the pancreas and liver,
8. deficient circulation of the scalp, hair loss,
9. disorders of the airways, including bronchial asthma,
10. metabolic disorders,
11. spasmogenic disorders of the uterus,
12. incontinence.

Furthermore, the compounds according to the invention promote the circulation of the scalp and hair growth. They are also tocolytically active.

The compounds according to the invention have a long duration of action accompanied by only minor toxicity. They are therefore suitable in particular for the treatment of acute and chronic cardiac diseases, for the therapy of high blood pressure, cardiac insufficiency and also for the treatment of asthma and cerebral and peripheral circulatory disturbances.

The compounds of the present invention may be used in the human orally or parenterally in a dosage of 0.001 to 100 mg, preferably 0.01 to 50 mg, particularly preferably 0.05 to 10 mg per day, particularly also in subdivided doses, for example twice to four times daily. These dosages are advantageous for the treatment of the diseases previously mentioned, in particular cardiac diseases, hypertonia, asthma and circulatory disturbances.

In general, it has proved advantageous on intravenous administration to administer amounts of about 0.001 to 10 mg, preferably about 0.05 to 5 mg, to the human per day to attain effective results. On oral administration, the dosage is about 0.05 to 30 mg, preferably 0.1 to 10 mg per day in the human.

The dosages previously mentioned are particularly preferred for the treatment of hypertonia.

In spite of this it may be necessary to depart from the amounts mentioned, in particular depending on the body weight or the type of the administration route, but also because of the individual behavior towards the medicament or the manner of its formulation and the point in time or interval at which the administration takes place. Thus, in some cases it may be sufficient to manage with less than the minimum amount previously mentioned, whereas in other cases the upper limit mentioned must be exceeded. In the case of the administration of larger amounts, it may be advisable to divide these into a number of individual doses over the day.

The invention also relates to the compounds according to the invention for the treatment of the preceding diseases and methods for the treatment of these diseases in which these compounds are used and also their use in methods for the production of agents which contain these compounds, for the treatment of these diseases and methods for the preparation of the compounds.

According to the invention, pharmaceutical preparations or compositions are provided which contain one compound according to the invention or its pharmaceutically tolerable salt or acid addition salts together with a pharmaceutically tolerable diluent or excipient.

The compounds according to the invention can be mixed with the customary pharmaceutically tolerable diluents or excipients and, if appropriate, with other auxiliaries and, for example, administered orally or parenterally. They may preferably be administered orally in the form of granules, capsules, pills, tablets, film tablets, coated tablets, syrups, emulsions, suspensions, dispersions, aerosols and solutions as well as liquids or parenterally in the form of solutions, emulsions or suspensions. Preparations to be administered orally may contain one or more additives such as sweeteners, flavorings, colorants and preservatives. Tablets may contain the active compound mixed with customary pharmaceutically tolerable auxiliaries, for example inert diluents such as calcium carbonate, sodium carbonate, lactose and talc, granulating agents and agents which promote the disintegration of the tablets on oral administration such as starch or alginic acid, binders such as starch or gelatin, lubricants such as magnesium stearate, stearic acid and talc.

Suitable excipients are, for example, milk sugar (lactose), gelatin, maize starch, stearic acid, ethanol, propylene glycol, ethers of tetrahydrofurfuryl alcohol and water.

Examples of auxiliaries which may be mentioned are:

Water, non-toxic organic solvents, such as paraffins (for example mineral oil fractions), vegetable oils (for example groundnut/sesame oil), alcohols (for example ethyl alcohol, glycerol), glycols (for example propylene glycol, polyethylene glycol), solid excipients, such as, for example, ground natural minerals (for example kaolins, aluminas, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkylsulphonates and arylsulphonates), dispersants (for example lignin-sulphite waste liquors, methylcellulose, starch and polyvinylpyrrolidone) and lubricants (for example magnesium stearate, talc, stearic acid and sodium lauryl sulfate).

The formulations are prepared, for example, by extending the active compounds with solvents and/or excipients, if appropriate using emulsifiers and/or dispersants, it being possible, for example, in the case of the use of water as a diluent to use, if appropriate, organic solvents as auxiliary solvents.

Administration is carried out in a customary manner, preferably orally or parenterally, in particular perlingually or intravenously. In the case of oral administration, tablets may of course also contain additives, such as sodium citrate, calcium carbonate and dicalcium phosphate together with various additives, such as starch, preferably potato starch, gelatin and the like in addition to the excipients mentioned. Furthermore, lubricants such as magnesium stearate, sodium lauryl sulfate and talc may additionally be used for tableting. In the case of aqueous suspensions and/or elixirs, which are intended for oral administration, various flavor enhancers or colorants may be added to the active compounds in addition to the abovementioned auxiliaries.

In the case of parenteral administration, solutions of the active compounds using suitable liquid excipients may be employed.

The tablets can be coated by known procedures in order to delay disintegration and absorption into the gastrointestinal tract, as a result of which the activity of the active compound may be extended over a relatively long period of time. Similarly, in the suspensions, the active compound may be mixed with auxiliaries which are customary for the preparation of such compositions, for example suspending agents such as methylcellulose, tragacanth or sodium alginate, wetting agents such as lecithin, polyoxyethylene stearate and polyoxyethylene sorbitan monooleate and preservatives such as ethyl parahydroxybenzoate. Capsules may contain the active compound as a single constituent or mixed with a solid diluent such as calcium carbonate, calcium phosphate or kaolin. The injectable preparations are likewise formulated in a manner known per se.

The pharmaceutical preparations may contain the active compound in an amount from 0.1 to 90 per cent by weight, in particular 1 to 90 per cent by weight, i.e. in amounts which are sufficient in order to achieve the dosage range indicated, the remainder being an excipient or additive. In respect of preparation and administration, solid preparations such as tablets and capsules are preferred. Preferably, the preparations contain the active compound in an amount from 0.05 to 10 mg.

The compounds of the formula I are accessible by nucleophilic ring opening of 2,2,6-substituted 3,4-dihydro-3,4-epoxy-2H-benzo[b]pyrans of the formula II

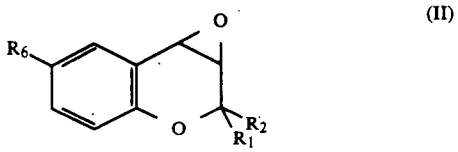

(II)

Ammonia, primary and secondary organic amines, salts and esters of alpha-omega-aminocarboxylic acids and anions of cyclic amides and cyclic urea, carbamic acid, thiocarbamic acid or cyanoguanidine derivatives are preferably employed as nucleophiles. The compounds of the formula I resulting from this are obtained as transisomers and are virtually free of cis-isomers.

As secondary amines, the heterocycles H-A and H-B are in particular employed, and as cyclic amides the heterocycle C is employed as the anion which is obtainable by action of a strong base.

As the cyclic urea, carbamic acid or thiocarbamic acid derivative, the heterocycle D is employed, after the anion thereof has been generated by action of a strong base. The heterocycle E, in which p, Y and Z have the abovementioned meaning, is employed in the form of its anion, which is obtainable using a strong base.

The following preparation processes are preferred:

A subgroup (1) of compounds of the formula I, in which $R_6$ stands for the substituent class $R_6'$, $R_5$ stands for the heterocyclic radicals A and B, $R_3$ stands for hydroxyl and R. stands for hydrogen and $R_1$ and $R_2$ have the abovementioned meaning, can be prepared by reaction of compounds of the general formula IIa

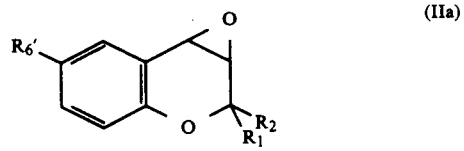

(IIa)

with heterocycles of the general formula H-A or H-B, in which A and B have the abovementioned meaning.

The compounds of the formula H-A or H-B are known or can be prepared in analogy to known methods.

The reaction of the oxirane IIa can be carried out at temperatures between $-10°$ C. and $+200°$ C., but preferably at room temperature or slightly elevated temperature, for example 20°–100° C.

The reaction is preferably carried out in an alcohol, such as methanol, ethanol or propanol or in a lower ketone such as acetone or butanone or in a suitable ether such as dioxane or without solvents, expediently at the reflux temperature of the reaction mixture, if a solvent is present. Compounds of the formula I result in which $R_3$ having the meaning hydroxyl and $R_5$ having the meaning A or B are arranged stereospecifically trans to one another.

Another subgroup (2) of compounds of the formula I, in which $R_1$ and $R_2$ have the abovementioned meaning, $R_3$ stands for hydroxyl, $R_4$ stands for hydrogen, $R_6$ stands for $R_6'$ with the abovementioned meaning and $R_5$ stands for the heterocyclic radicals C and D, in which k, m, n and Y have the abovementioned meaning and X stands for oxygen, are obtained from oxiranes of the formula IIa, in which $R_1$, $R_2$ and $R_6'$ have the abovementioned meaning, and heterocycles of the structure H-C and H-D, where k, m, n and Y have the abovementioned meaning and X stands for oxygen.

The reaction of the oxirane IIa with the group of heterocycles H-C and H-D described above is carried out in a solvent such as dimethyl sulphoxide in the presence of a base such as sodium hydride at temperatures between 0° and 80° C., preferably at room temperature.

The heterocycles of the formula H-C are known, those of the formula H-D are known or can be prepared in analogy to known methods, inter alia as described in J. Med. Chem. 24, 1089-92 (1981).

Heterocycles of the formula H-D, in which m is 1 or 2 and k is 1 or 2, with the proviso that m+k is 1, 2 or 3 and Y has the meaning unsubstituted amino, are expediently converted into derivatives having a protected amino group, before they are reacted under the abovementioned conditions with oxiranes IIa.

It is possible for such a protective group for the protected amino groups to be the abovementioned radicals $R_7$, but in particular benzyl, benzylcarbonyl, phenylcarbonyl, t-butyloxycarbonyl, benzyloxycarbonyl, $C_{1-2}$-alkylcarbonyl or triphenylmethyl, and it is removed by hydrogenolysis or hydrolysis after reaction with oxiranes of the formula IIa has taken place under the conditions most favorable in each case for the protective group concerned, if this is desired. Of the abovementioned protective groups, acetyl and benzyl are preferred.

Compounds of the subgroup (2), in which $R_5$ stands for C, X stands for oxygen and n stands for 2 or 3, are additionally accessible by cyclization of open-chain precursors in analogy to the methods described in EP 0,076,075.

Starting from compounds of the subgroup (2), a further subgroup (3) of compounds of the formula I, in which $R_1$ and $R_2$ have the abovementioned meaning, $R_3$ stands for hydroxyl, $R_4$ stands for hydrogen, $R_6$ stands for $R_6'$ having the abovementioned meaning and $R_5$ stands for the heterocyclic radicals C and D, in which k, m, n and Y have the abovementioned meaning, but X stands for sulphur, are accessible by reaction of compounds of the subgroup (2) with sulphurization reagents such as hydrogen sulfide, phosphorus pentasulfide or Lawesson's reagent (p-methoxyphenylthiophosphine sulfide, dimer).

The sulphurization reaction is carried out under the conditions customary for the reagent concerned, for example hydrogen sulfide is preferably reacted under acid catalysis (for example using hydrogen chloride) in a polar solvent such as acetic acid or ethanol.

The reaction with Lawesson's reagent is preferably carried out under reflux temperature in a dry solvent such as methylene chloride or toluene.

Another subgroup (4) of compounds of the formula I, in which $R_1$ and $R_2$ have the abovementioned meaning, $R_3$ stands for hydroxyl, $R_4$ stands for hydrogen and $R_6$ stands for both substituent classes $R_6'$ and $R_6''$ with the meaning indicated for $R_6'$ and $R_6''$ and $R_5$ has the meaning E, is accessible from compounds of the general formula IIa and IIb by reaction with heterocycles of the formula H-E, in which E has the meaning indicated:

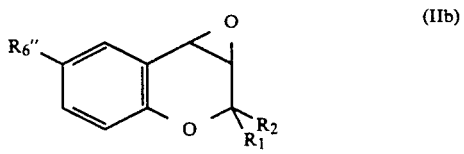

The heterocycles of the formula H-E are known or can be prepared by known methods which are described, for example, in J. Heterocycl. Chem. 19, 1205 (1982), ibid 24, 275 (1987), DE 2,205,745, Helv. Chim. Acta 67, 1669 (1984), Can. J. Chem. 39, 1787 (1961), EP 0,277,317 or Chem. Ber. 100, 591 (1967).

The reaction of IIa and IIb with H-E is carried out in solvents such as dimethyl sulphoxide in the presence of a base such as sodium hydride under the conditions described for subgroup (2).

Alternatively, compounds of the abovementioned subgroup (4), in which Z has the meaning =N—CN, can be prepared from compounds of the subgroup (3), in which $R_1$, $R_2$ and $R_6'$ have the meaning indicated, $R_3$ stands for hydroxyl, $R_4$ stands for hydrogen and $R_5$ stands for the radical D, in which k, m, n and Y have the meaning indicated and X stands for sulphur, or from analogous compounds, in which $R_6$ has the meaning $R_6''$ and which are described in EP 0,107,423, by reaction with lead cyanamide PbNCN in a solvent such as ethanol or dimethyl sulphoxide at temperatures between 20° C. and the reflux temperature of the solvent used, preferably at the reflux temperature of the solvent used.

The compounds of the subgroups (1)–(4) described previously contain a free hydroxyl group $R_3$ and can therefore be converted, if they contain no reactive unsubstituted amino group, i.e. if Y in formula D does not stand for unsubstituted amino and Y in formula D only stands for unsubstituted amino if m is simultaneously 0, by O-alkylation or O-acylation into another subgroup (5) of compounds of the formula I, in which $R_3$ has the meaning $C_{1-6}$-alkoxy or $C_{1-8}$-alkylcarbonyloxy, formyloxy, $C_{1-8}$-monoalkylaminocarbonyloxy or $C_{1-8}$-dialkylaminocarbonyloxy, $R_1$ and $R_2$ have the meaning indicated, $R_4$ stands for hydrogen and $R_6$ stands for $R_6'$, if $R_5$ has the meaning (A), (B), (C) or (D) and stands for $R_6'$ or $R_6''$, if $R_5$ has the meaning (E).

Compounds of the subgroup (5), in which $R_5$ has the meaning B or D and Y stands for unsubstituted amino, are accessible by 0-alkylation or 0-acylation of compounds of the subgroup (1), (2) or (3), in which Y has the meaning substituted amino —$NR_7$—, by subsequent elimination of the protective group $R_7$ as described for subgroup (2).

An alkylation can be carried out, for example, by using a $C_{1-6}$-alkyl iodide in an inert solvent such as toluene or dimethylformamide in the presence of a base such as potassium hydroxide or barium oxide.

An esterification can be carried out by using a $C_{1-8}$-acyl chloride or acyl anhydride or another activated derivative of the alkanoic acid concerned, if appropriate in the presence of an organic base such as pyridine or triethylamine or an inorganic base such as potassium carbonate, if appropriate with the assistance of catalysts such as 4-(N,N-dimethylamino)pyridine or condensation reagents such as dicyclohexylcarbodiimide in an inert solvent, if appropriate at elevated temperature.

A reaction to give carbonates is carried out analogously by reaction with chloroformic acid $C_{1-8}$-alkyl esters under the abovementioned conditions.

The reaction to give carbamates is carried out either in analogy to the method described above by reaction with mono- or dialkylaminocarbamoyl chlorides or by reaction with $C_{1-8}$-alkyl isocyanates in an inert solvent, for example toluene, at temperatures between 0° C. and the boiling temperature of the reaction mixture.

Formyloxy can be introduced by reaction with formic acid in the presence of pyridine.

Another subgroup (6) of compounds of the formula I, in which $R_3$ and $R_4$ together form a bond, $R_1$ and $R_2$ have the meaning indicated, $R_5$ stands for the radicals C, D and E and $R_6$ stands for $R_6'$, if $R_5$ stands for C, D and E or $R_6$ stands for $R_6'$ and $R_6''$, if $R_5$ stands for E, is accessible by dehydration of compounds of the subgroups (2), (3) and (4), in which $R_1$–$R_6$ have the meaning indicated there in each case.

The dehydration is carried out by means of reagents such as sodium hydride in an inert solvent such as tetrahydrofuran, preferably at reflux temperature of the reaction mixture. Compounds of the subgroup (6) may, if appropriate, be obtained as by-products in the reaction of oxiranes of the formula IIa with heterocycles of the formula H-C, H-D or H-E or in the reaction of oxiranes IIb with H-E, as a consequence of a further reaction of the hydroxyl compounds formed as intermediates of the subgroups (2) and (4) under the reaction conditions indicated for the subgroups (2), (3) and (4) concerned.

By reaction of oxiranes of the formula IIa with heterocycles of the formula H-C, H-D or H-E or of oxiranes IIb with H-E in a solvent such as dimethyl sulphoxide in the presence of a base such as sodium hydride at elevated temperature, preferably at 40° C., the compounds of the subgroup (6) can also be obtained directly, i.e. without isolation of intermediates of the subgroups (2) and (4), exclusively or as the principal product.

Mixtures of compounds of the subgroups (2) and (6) or (4) and (6) which may be obtained can be separated into the pure components by customary methods such as chromatography or crystallization.

Compounds of the general formula I, in which $R_1$ and $R_2$ have the meaning indicated, $R_3$ stands for hydroxyl or—as defined above—substituted hydroxyl and $R_4$ stands for hydrogen and R: stands for the heterocyclic radicals A, B, C, D and E defined above, where in the case of the radicals B, D and E, Y does not stand for sulphur and $R_6'$ has the meaning difluoromethylthio, trifluoromethylthio or 2,2,2-trifluoroethylthio, can be converted by suitable oxidizing agents such as, for example, hydrogen peroxide in glacial acetic acid or Oxone® in methanol-water mixtures at temperatures between 0° C. and the reflux temperature of the reaction mixture, preferably at temperatures between 20° and 60° C., into compounds of the formula I, in which $R_6$ has the meaning difluoromethylsulphinyl, difluoromethylsulphonyl, trifluoromethylsulphinyl, trifluoromethylsulphonyl, 2,2,2-trifluoroethylsulphinyl or 2,2,2-trifluoroethylsulphonyl. Mixtures of sulphinyl and sulphonyl compound which may be produced can be obtained pure by customary methods such as crystallization or chromatography.

By means of the process indicated for compounds of the subgroup (5), compounds of the general formula I, in which $R_1$ and $R_2$ have the abovementioned meaning, $R_3$ and $R_4$ together form a bond and $R_5$ and $R_6$ have the previous meaning, can be obtained from the compounds of the general formula I, in which $R_1$ and $R_2$ have the meaning indicated, $R_3$ stands for hydroxyl or hydrogen and $R_5$ stands for the heterocyclic radicals A, B, C, D and E defined above, with the proviso that in the radicals B, C and E, Y does not stand for sulphur, and $R_6'$ has the meaning difluoromethylsulphinyl, difluoromethylsulphonyl, trifluoromethylsulphinyl, trifluoromethylsulphonyl, 2,2,2-trifluoroethylsulphinyl and trifluoromethylsulphonyl, for example by treatment with sodium hydride in boiling tetrahydrofuran.

By means of the process indicated for compounds of the subgroup 5), compounds of the formula I, in which $R_3$ and $R_4$ together form a bond, where $R_1$, $R_2$ and $R_5$ have the abovementioned meaning, with the limitation that Y does not stand for sulphur and $R_6'$ has the meaning difluoromethylsulphinyl, difluoromethylsulphonyl, trifluoromethylsulphinyl, trifluoromethylsulphonyl, 2,2,2-trifluoroethylsulphinyl or 2,2,2-trifluoroethylsulphonyl, can be obtained from the compounds obtained by the process described previously by means of sodium hydride in tetrahydrofuran at reflux temperature of the reaction mixture.

Oxiranes of the formula IIa and IIb can be prepared—preferably in situ—from compounds of the formula IIIa and IIIb

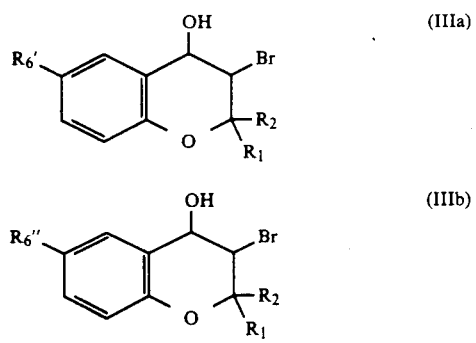

by reaction with a base such as sodium hydride in a solvent such as DMSO at temperatures between 0° and 80° C., preferably at 20°-25° C. In these cases, it is advantageous to add the heterocycles H-C, H-D and H-E to the reaction mixture only when oxirane formation is concluded.

If isolation of the oxirane IIa and IIb is desired, the reaction of the bromohydrins IIIa or IIIb can also be carried out in a suitable ether such as diethyl ether, dioxane or tetrahydrofuran using a base such as potassium hydroxide or sodium hydride or in aqueous mixtures of water-miscible ethers and a base such as potassium hydroxide. In these cases, the use of sodium hydride in tetrahydrofuran is preferred.

Compounds of the general formula IIIa and IIIb, in which the bromine atom and hydroxyl group are arranged trans to one another can be prepared by processes which are customary per se. One such process can be represented as follows and has been described many times, for example EP 0,076,075, J. Org. Chem. 38, (22), 3832 (1973), ibid. 39 (7), 881 (1974), ibid. 37 (6), 841 (1972):

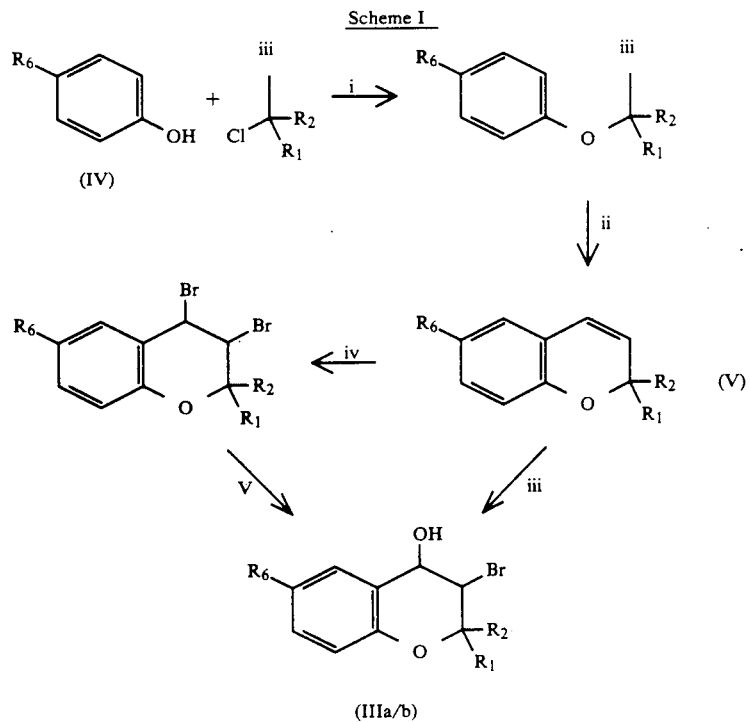

The following conditions are preferred:
i) for example $K_2CO_3$/acetone; reflux or $K_2CO_3$/butanone; reflux
or $K_2CO_3$/dimethylformamide, 90° C.
or NaOH/40% triethylbenzylammonium hydroxide in methanol; room temperature ii) for example 1,2-dichlorobenzene, 180° C.
or N,N'-diethylaniline, 200° C.
or without solvent, 200° C.

iii) N-bromosuccinimide/dimethylsulphoxide/water iv) bromine, tetrachloromethane v) acetone/water The 4-substituted phenols IV, in which $R_6$ has the abovementioned meaning, are known or can be prepared by known methods, for example by reduction of the corresponding 4-substituted nitroaromatics, for example using hydrogen and Raney nickel as the catalyst or by nascent hydrogen to give the corresponding 4-substituted anilines and diazotization and boiling of the latter to give the said 4-substituted phenols.

In cases in which $R_6$ has the meaning difluoromethylthio, difluoromethylsulphinyl, difluoromethylsulphonyl, trifluoromethylthio, trifluoromethylsulphinyl, trifluoromethylsulphonyl, 2,2,2-trifluoromethylthio, 2,2,2-trifluoroethylsulphinyl and 2,2,2-trifluoroethylsulphonyl, the radicals mentioned can frequently be introduced advantageously by chemical transformations of intermediates in which $R_6$ has a meaning other than the abovementioned meaning, for example 2H-benzo[b]pyrans of the general formula V, in which $R_6$ has the meaning difluoromethylsulphonyl, trifluoromethylsulphonyl and 2,2,2-trifluoroethylsulphonyl, are obtained by reaction of the corresponding fluoroalkylsulphonyl fluorides with 2H-benzo[b]pyrans of the general formula V, in which $R_6$ has the meaning MgHal, where Hal has the meaning chlorine, iodine and in particular, bromine.

Likewise, it is possible to react the Grignard compounds of 2H-benzo[b]pyrans described above with disulphides of the general formula R-S-S-R, in which R has the meaning trifluoromethyl, difluoromethyl and 2,2,2-trifluoroethyl, to give 2H-benzo[b]pyrans in which $R_6$ has the meaning difluoromethylthio, trifluoromethylthio and 2,2,2-trifluoroethylthio.

Furthermore, it is possible, starting from intermediates or final products in which $R_6$ contains a sulphur atom, to obtain intermediates or final products by methods which are customary per se by means of reduction and, in particular, oxidation, in which the designated sulphur atom has another oxidation level.

Possible oxidizing agents which may be mentioned by way of example are: potassium permanganate, sodium periodate, chromium trioxide or, preferably, Oxone ® (potassium monopersulphate) or hydrogen peroxide/glacial acetic acid.

Thus, for example, 4-difluoromethylsulphonylphenol, 4-trifluoromethylsulphonylphenol or 4-(2,2,2-trifluoroethylsulphonyl)phenol can be obtained more conveniently than by known methods by oxidation of the corresponding fluoroalkylthiophenols with Oxone ® in methanol-water mixtures at temperatures between −10° C. and the reflux temperature of the reaction mixture, preferably at temperatures between 0° C. and 25° C.

Particularly in cases in which $R_6$ has the meaning difluoromethylsulphinyl, trifluoromethylsulphinyl or 2,2,2-trifluoroethylsulphinyl, it is more convenient, starting from the corresponding 4-fluoroalkylthiophenols according to scheme I, first to prepare the corresponding 6-fluoroalkyl-2H-benzo[b]pyrans V, in which $R_1$ and $R_2$ have the abovementioned meaning, and then to carry out the desired oxidation to the respective 6-fluoroalkylsulphinyl-2H-benzo[b]pyrans of the general formula V, in which $R_6$ has the abovementioned meaning. Surprisingly, the selectivity of this reaction is very high with the classes of compound mentioned.

The starting materials used are known or can be prepared by processes which are known per se or are analogous to those described here or can be prepared analogously to processes known per se.

The compounds of the formula I may be both bases and acids or may be amphoteric and are therefore isolated from the reaction mixtures in the form of their salts or acid addition salts. As bases, they can be converted into salts by known methods using suitable inorganic or organic acids or, as acids, form salts with bases.

Physiologically tolerable salts or acid addition salts are preferred. In this connection, for example, sulfuric acid or hydrohalic acids, for example hydrochloric acid, are suitable as inorganic acids, and, for example, fumaric acid, maleic acid, citric acid and tartaric acid are suitable as organic acids. For preparation, the alcoholic solution of a suitable acid is added to the hot alcoholic solution of the base and the salt is obtained after addition of ether. Preferred salts are the alkali metal, alkaline earth and ammonium salts of the compounds of the formula I, which are obtained with the corresponding bases, in particular sodium hydroxide or potassium hydroxide.

The compounds of the formula I according to the invention may have chiral centers and may, depending on the substituents, possess further asymmetric sulphur or carbon atoms and therefore exist as racemates and diastereoisomers. On account of the physicochemical differences of their constituents, diastereoisomers may be separated into their racemic modifications in a known manner. Racemates may be separated by known methods, for example by recrystallizing in optically active solvents, by means of microorganisms or reaction with an optically active acid or base which forms a salt with the racemic compound, separation of the diastereoisomers by fractional crystallization and liberation of the enantiomers by suitable agents. Particularly suitable optically active acids are, for example, the d- and l-forms of tartaric acid, ditoluyltartaric acid, malic acid, mandelic acid, camphorsulphonic acid or pyrrolidonecarboxylic acid. Suitable optically active bases are alphaphenylethylamine, menthylamine, ephedrine, brucine and quinine. Advantageously, the more active of the antipodes is isolated. However, according to the invention it is also possible to obtain the pure enantiomers by asymmetric synthesis.

The following preparation processes are particularly preferred:

Process for the preparation of the compounds according to claim 1, characterized in that a) oxiranes of the general formula IIa, in which $R_1$, $R_2$ and $R_6'$, have the abovementioned meaning, are reacted with anions C⁻ and D⁻ of heterocycles of the general formula H-C and H-D, in which X has the meaning oxygen and Y, k, m and n have the abovementioned meaning, with the limitation that for any heterocycles H-D for which m is unequal to 0 applies, Y does not stand for unsubstituted amino, to give compounds of the general formula I, in which $R_1$, $R_2$ and $R_6'$ have the abovementioned meaning, $R_3$ stands for hydroxyl, $R_4$ stands for hydrogen and $R_5$ stands for the heterocyclic radicals C and D, in which X stands for oxygen and Y, k, m and n have the above-mentioned meaning, with the exception that Y does not stand for unsubstituted amino if m is unequal to 0, where the substituents $R_3$ and $R_5$ of the compounds of the formula I are arranged trans to one another and in that b) any compounds according to the invention as in a) for which Y stands for substituted amino and m stands for 1 or 2 are converted by hydrolysis, hydrogenolyses or dealkylation into compounds of the formula I as in a), in which Y then also stands for unsubstituted amino if m is unequal to 0, where $R_3$ and $R_5$ in turn are arranged trans to one another and in that c) oxiranes of the general formula IIa as in a) are reacted with amines of the general formula H-A and H-B to give compounds of the formula I, in which $R_1$, $R_2$ and $R_6'$ have the abovementioned meaning and $R_5$ stands for A or B having the abovementioned meaning for n and Y, $R_4$ stands for hydrogen and $R_3$ stands for hydroxyl, where $R_3$ and $R_5$ are arranged trans to one another and in that d) oxiranes of the general formula IIa and IIb, in which $R_1$, $R_2$, $R_6'$ and $R_6''$ have the above-mentioned meaning, are reacted with anions $E^-$ of heterocycles of the general formula H-E, in which Y, Z and p have the above-mentioned meaning, to give compounds of the general formula I, in which $R_1$, $R_2$, $R_6'$ and $R_6''$ have the abovementioned meaning, $R_3$ stands for hydroxyl, $R_4$ stands for hydrogen and $R_5$ stands for E having the meaning indicated for Y, Z and p, where $R_3$ and $R_5$ are arranged trans to one another and in that e) compounds of the formula I according to the invention as in a) and b) are reacted with sulphurization reagents, for example, preferably Lawesson's reagent in an inert solvent such as, for example, toluene to give compounds of the formula I, in which $R_1$, $R_2$, $R_3$, $R_4$ and $R_6'$ are as defined under a), $R_5$ stands for the radicals C and D having the meaning indicated for Y, k, m and n, where, however, X stands for sulphur, and in that f) compounds of the formula I according to the invention as in a), d) and e), and any compounds according to the invention as in c), in which Y does not stand for unsubstituted amino, are converted by reaction with alkyl halides, mesylates, brosylates or tosylates, acyl halides, anhydrides, imidazolides, alkylcarbonyl halides or anhydrides, mono- or dialkylaminocarbonyl halides, phosgene or alkyl isocyanates into compounds of the general formula I, in which $R_1$, $R_2$, $R_4$, $R_6'$, $R_6''$ and $R_5$ are defined as in a), c), d) and e), with the limitation that Y in the radical B does not stand for unsubstituted amino, and $R_3$ stands for $C_{1-6}$-alkoxys, formyloxy, $C_{1-8}$-alkylcarbonyloxy, $C_{1-8}$-monoalkylamino or $C_{1-8}$-dialkylamino, and in that g) any compounds of the formula I according to the invention as in f), in which Y stands for substituted, in particular benzyl-substituted amino, are converted by suitable measures, in particular hydrogenolysis into compounds of the formula I as in f), in which Y stands for unsubstituted amino and in that h) compounds of the formula I according to the invention as in a), b), d) and e) are reacted in the presence of a dehydrating agent such as, for example, sodium hydride in an inert solvent such as, for example, tetrahydrofuran to give compounds of the general formula I, in which $R_1$, $R_2$, $R_5$, $R_6'$ and $R_6''$ have the abovementioned meaning and $R_3$, together with $R_4$, forms a bond and in that i) oxiranes of the general formulae IIa or IIb, in which $R_1$, $R_2$ and $R_6'$ and $R_6''$ have the above-mentioned meaning are reacted in the presence of at least two equivalents of a base first to give compounds according to the invention as in a) and d), but these are not isolated but, by lengthening the reaction time and, in particular, by increasing the reaction temperature, preferably to 40° C., are converted in situ into compounds according to the invention as in h) and these are isolated by customary methods and in that j) any compounds according to the invention as in a), b), c), d), f), g) and h), in which $R_6'$ has the meaning difluoromethylthio, trifluoromethylthio and 2,2,2-trifluoroethylthio and at the same time X and Y have a meaning other than sulphur, are converted using suitable oxidizing agents, preferably Oxone ® or hydrogen peroxide/glacial acetic acid into any compounds according to the invention as in a), b), c), d), g) and h), in which $R_6'$ has the meaning difluoromethylsulphinyl, trifluoromethylsulphinyl, 2,2,2-trifluoroethylsulphinyl and, in particular, trifluoromethylsulphonyl, 2,2,2-trifluoroethylsulphonyl or difluoromethylsulphonyl, or mixtures of sulphinyl and sulphonyl compound which may be obtained are separated into the pure components by methods which are customary per se.

The following examples are intended to illustrate the invention:

Example 1

6-Cyano-3,4-dihydro-2,2-dimethyl-trans-4-(2-cyanimino-3-imidazolidin-1-yl)-2H-benzo(b)pyran-3-ol

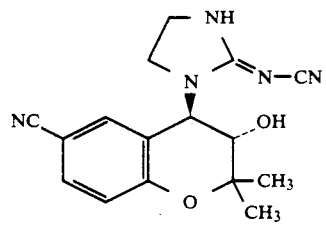

Method A 2.41 g (0.012 mol) of 6-cyano-3,4-dihydro-3,4-oxiranyl- 2,2-dimethyl-2H-benzo(b)pyran and 1.76 g (0.016 mol) of 2-cyaniminoimidazolidine are dissolved in 25 ml of dry dimethyl sulphoxide and 0.38 g (0.016 mol) of oil-free sodium hydride is added in portions so that the temperature does not exceed 25° C. The mixture is stirred for 72 hours at room temperature under a protective gas atmosphere and hydrolysed cautiously using 80 ml of water. The crystals deposited are washed with water, dried and recrystallized from diisopropyl ether.

Yield: 1.12 g (30 % of theory) of 6-cyano-3,4-dihydro-2,2-dimethyl-trans-4-(2-cyanimino-3-imidazolidin-1-yl)-2H-benzo(b)pyran-3-ol).

m.p. 250° C. (dec.).

Method B

The water phase obtained as in method A after hydrolysis is extracted using ethyl acetate (3×100 ml) and the combined phases are concentrated. The residue is taken up in toluene, the organic phase is washed with water (3×100 ml), dried over sodium sulfate and concentrated. The residue is recrystallized (ethyl acetate/diisopropyl ether) or purified by column chromatography (silica gel Si 60, chloroform/methanol 95:5) and the compound of Example 1 is obtained.

The compounds of Examples 2, 3, 8, 10 to 22, 26, 28 to 30, 32, 35, 37 to 40, 42 and 46 to 48 were obtained analogously by method A or B (see Table 1) from the corresponding epoxide and the corresponding amide, carbamate, thiocarbamate, urea, cyanoguanidine or nitromethylidene heterocycle.

EXAMPLE 4

6-Difluoromethoxy-3,4-dihydro-2,2-dimethyl-trans-4-(1-pyrrolidinyl]-2H-benzo(b)pyran-3-ol

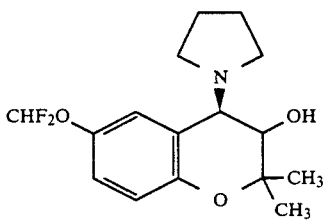

Method C 2.42 g (10 mmol) of 6-difluoromethoxy-3,4-dihydro--3,4-oxiranyl-2,2-dimethyl-2H-benzo(b)pyran and 0.85 g (12 mmol) of pyrrolidine are held at reflux temperature for 20 hours in 30 ml of dry ethanol. The solvent is then removed in vacuo, hexane is added to the residue and the product is precipitated as the hydrochloride using ethereal HCl solution. 350 mg of colorless crystals (10 % of theory) of 6-difluoromethoxy-3,4-dihydro--2,2-dimethyl-trans-4-(1-pyrrolidinyl)-2H-benzo(b)pyran-3-ol are obtained.
m.p. 176°-178° C.

Example 6 and Example 7 were obtained analogously. The compound of Example 7 was recrystallized from hexane/ether as the free base.

Example 5

6-Cyano-2,2-dimethyl-(2-cyanimino-3-thiazolidin-1-yl)-2H-
benzo(b)pyran

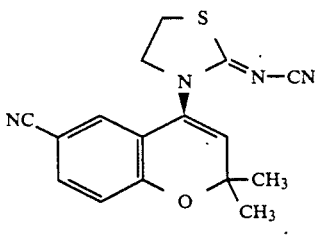

2.41 g (0.012 mol]of 6-cyano-3,4-dihydro-3,4-oxiranyl-2,2-dimethyl-2H-benzo(b)pyran and 2.03 g (0.016 mol) of 2-cyanimino-thiazolidine were reacted, as described above, with 0.38 g (0.016 mol) of sodium hydride in DMSO at 45° C. After 100 hours, the mixture was hydrolyzed and worked up according to method B. 186 mg of colorless crystals of 6-cyano-2,2-dimethyl-(2-cyanimino-3-thiazolidin-1-yl)-2H-benzo(b)pyran are obtained, m.p. 230°-232° C. (yield: 5 % of theory).

Example 9, 25, 27, 31, 33, 34, 36, 41 and 43 were obtained analogously (see Table 1).

Example 8

6-Difluoromethoxy-3,4-dihydro-2,2-dimethyl-trans-4-(2-oxo-1-piperidinyl)-2H-benzo(b)pyran-3-ol

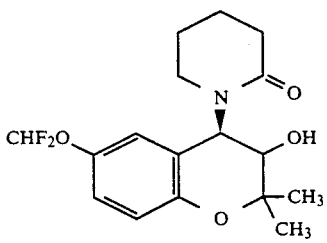

2.78 g (0.012 mol) of 6-difluoro-3,4-dihydro-3,4-oxiranyl-2,2-dimethyl-2H-benzo(b)pyran were reacted with 1.58 g (0.016 mol) of 2-oxopiperidine according to method A. 2.05 g of 6-difluoromethoxy-3,4-dihydro-2,2-dimethyl-trans-4-(2-oxo-1-piperidinyl)-2H-benzo(b)pyran-3-ol are obtained as colorless crystals, m.p. 165° C (yield 50 % of theory).

Example 19

6-Trifluoromethylsulphinyl-3,4-dihydro-2,2-dimethyl-trans-4-(2-oxo-1-piperidinyl)-2H-benzo(b)pyran-3-ol The epoxide described (Example 13') is reacted with 2-piperidinone according to method A and worked up according to method B.

Yield: 1.1 g (42 % of theory) of the compound mentioned in the heading.

Example 22 and 19

-Trifluoromethylsulphonyl-3,4-dihydro-2,2-dimethyl-trans-4-(2-oxo-1-piperidinyl)-2H-benzo(b)pyran-3-ol
and
-trifluoromethylsulphinyl-3,4-dihydro-2,2-dimethyl-trans-4-(2-oxo-1-piperidinyl)-2H-benzo(b)pyran-3-ol 0.2 g (5.3 mmol) of 6-trifluoromethylthio-3,4-,4-dihydro-2,2-dimethyl-trans-4-(2-oxo-1-piperidinyl)-2H-benzo(b)pyran-3-ol are dissolved in 7 ml of methanol and a suspension of 1 g of Oxone ® in 5 ml of water is added at 0° C. with stirring. After stirring for 5 days at room temperature, the mixture is diluted using 20 ml of water and extracted using chloroform (50 ml). After drying and evaporating, 220 mg of white crystals remain. By means of HPLC (eluent 98 : 2 chloroform:methanol), 140 mg (64 % of theory) of 6-trifluoromethylsulphonyl-3,4-dihydro-2,2-dimethyl-trans-4-(2-oxo-1-piperidinyl)-2H-benzo(b)pyran-3ol and 15 mg (7 % of theory) of 6-trifluoromethylsulphinyl-3,4-dihydro-2,2-dimethyl-trans-4-(2-oxo-1-piperidinyl)-2H-benzo(b)pyran-3-ol are obtained.

Example 24

6-Difluoromethoxy-3,4-dihydro-2,2-dimethyl-trans-4-(2-oxo-4-piperazin-1-yl)-2H-benzo( )pyran-3-ol

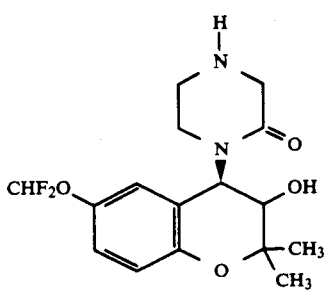

1.77 g (4.1 mmol) of compound no. 165 of Example 28 were dissolved in 100 ml of methanol/water/glacial acetic acid (83/15/2) and hydrogenated in an autoclave with the addition of 200 mg of Pearlman's catalyst for 3.5 hours at room temperature and at a hydrogen pressure of 10 bar. The catalyst was filtered off, and the filtrate was concentrated and treated with ethanolic hydrogen chloride solution. After evaporating, the residue was recrystallized from acetone. 1.2 g of colorless crystals of 6-difluoromethoxy-3,4-dihydro-2,2-dimethyl-trans-4-(2-oxo-4-piperazin-1-yl)-2H-benzo(b)pyran-3-ol are obtained, m.p. 240° C. (dec.), (yield 77.5 % of theory).

Example 32 and 44

6-Trifluoromethylsulphonyl-3,4-dihydro-2,2-dimethyl-trans-4-(2-oxo-1-pyrrolidinyl)-2H-benzo(b)pyran-3-ol
and
6-trifluoromethylsulphinyl-3,4-dihydro-2,2-dimethyl-trans-4-(2-oxo-1-pyrrolidinyl)-2H-benzo(b)pyran-3-ol 0.2 g (5.5 mmol) of 6-trifluoromethylthio-3,4-dihydro-2,2-dimethyl-trans-4-(2-oxo-1-pyrrolidinyl)-2H-benzo(b)pyran-3-ol are dissolved in 7 ml of methanol and a suspension of 1 g of Oxone ® in 5 ml of water is added at 0° C. with stirring. After stirring for 5 days at room temperature, the mixture is diluted using 20 ml of water and extracted using chloroform (3×50 ml). After drying and evaporating, 0.2 g of white crystals remain. By means of HPLC (eluent chloroform:methanol 98 : 2), 120 mg (55 % of theory) of 6-trifluoromethylsulphonyl-3,4-dihydro-2,2-dimethyl-trans-4-(2-oxo-1-pyrrolidinyl)-2H-benzo(b)pyran-3-ol and 15 mg of 6-trifluoromethylsulphinyl-3,4-dihydro-2,2-dimethyl-trans-4-(2-oxo-1-pyrrolidinyl)-2H-benzo(b)-pyran-3-ol are obtained.

Example 44

6-Trifluoromethylsulphinyl-3,4-dihydro-2,2-dimethyl-trans-4-(2-oxo-1-pyrrolidinyl)-2H-benzo(b)pyran-3-ol The epoxide described above (Example 13') was reacted with 2-pyrrolidinone according to method A and worked up according to method B. Yield: 1.2 g (48 % of theory) of the compound mentioned in the heading.

TABLE 1

| Example | Method | Reaction time | Yield | m.p. |
|---|---|---|---|---|
| 6-Cyano-3,4-dihydro-2,2-dimethyl-trans-4-(2-cyanimino-3-imidazolidin-1-yl)-2H-benzo[b]pyran-3-ol | | | | |
| 1 | A | 72 h | 30% | 250° C. |
| 6-Difluoromethoxy-3,4-dihydro-2,2-dimethyl-trans-4-(2-oxo-1-pyrrolidinyl)-2H-benzo[b]pyran-3-ol | | | | |
| 2 | A | 48 h | 50% | 157–8° C. |
| 6-Difluoromethoxy-3,4-dihydro-2,2-dimethyl-trans-4-(2-oxo-3-imidazolidin-1-yl)-2H-benzo[b]pyran-3-ol | | | | |
| 3 | A | 30 h | 12% | 222° C. |

6-Difluoromethoxy-3,4-dihydro-2,2-dimethyl-trans-4-(1-

TABLE 1-continued

| Example | | Method | Reaction time | Yield | m.p. |
|---|---|---|---|---|---|
| pyrrolidinyl)-2H-benzo[b]pyran-3-ol | | | | | |
| 4 | [structure: 6-difluoromethoxy-3,4-dihydro-2,2-dimethyl-trans-4-(1-pyrrolidinyl)-2H-benzo[b]pyran-3-ol] | C | 20 h | 10% (as hydrochloride) | 176–8° C. |
| 6-Cyano-2,2-dimethyl-4-(2-cyanimino-3-thiazolidin-1-yl-2H-benzo[b]pyran | | | | | |
| 5 | [structure] | B | 100 h | 5% | 230–2° C. |
| 6-Difluoromethoxy-3,4-dihydro-2,2-dimethyl-trans-4-(1-piperidinyl)-2H-benzo[b]pyran-3-ol | | | | | |
| 6 | [structure] | C | 20 h | 40% (as hydrochloride) | 168–71° C. |
| 6-Difluoromethoxy-3,4-dihydro-2,2-dimethyl-trans-4-(1-N-morpholinyl)-2H-benzo[b]pyran-3-ol | | | | | |
| 7 | [structure] | C | 20 h | 75% | 138–9° C. |
| 6-Difluoromethoxy-3,4-dihydro-2,2-dimethyl-trans-4-(2-oxo-1-piperidinyl)-2H-benzo[b]pyran-3-ol | | | | | |
| 8 | [structure] | A | 48 h | 50% | 165° C. |
| 6-Cyano-2,2-dimethyl-4-(2-cyanimino-3-N-methylimidazolidin-1-yl)-2H-benzo[b]pyran | | | | | |

TABLE 1-continued

| Example | | Method | Reaction time | Yield | m.p. |
|---|---|---|---|---|---|
| 9 | [structure: 6-cyano-chromene with 2,2-dimethyl, 4-(3-methyl-2-cyanimino-imidazolidin-1-yl) substituent] | A | 20 h | 11% | 227° C. |
| 10 | 6-Difluoromethoxy-3,4-dihydro-2,2-dimethyl-trans-4-(2-oxo-3-oxazolidin-1-yl)-2H-benzo[b]pyran-3-ol [structure] | B | 72 h | 35% | 171–2° C. |
| 11 | 6-Difluoromethoxy-3,4-dihydro-2,2-dimethyl-trans-4-(2-oxo-3-N-methylimidazolidin-1-yl)-2H-benzo[b]pyran-3-ol [structure] | B | 72 h | 38% | 190–1° C. |
| 12 | 6-Cyano-3,4-dihydro-2,2-dimethyl-trans-4-(2-cyanimino-3-hexahydropyrimidin-1-yl)-2H-benzo[b]pyran-3-ol [structure] | A | 48 h | 45% | 274° C. |
| 13 | 6-Difluoromethoxy-3,4-dihydro-2,2-dimethyl-trans-4-(2-cyanimino-3-hexahydropyrimidin-1-yl)-2H-benzo[b]pyran-3-ol [structure] | B | 60 h | 8% | 235–8° C. |
| 14 | 6-Difluoromethoxy-3,4-dihydro-2,2-dimethyl-trans-4-(2-cyanimino-3-thiazolidin-1-yl)-2H-benzo[b]pyran-3-ol [structure] | B | 48 h | 10% | 194° C. |

TABLE 1-continued

| Example | Method | Reaction time | Yield | m.p. |
|---|---|---|---|---|
| 6-Difluoromethoxy-3,4-dihydro-2,2-dimethyl-trans-4-(2-oxo-3-N-phenylimidazolidin-1-yl)-2H-benzo[b]pyran-3-ol 15 | B | 48 h | 10% | 186° C. |

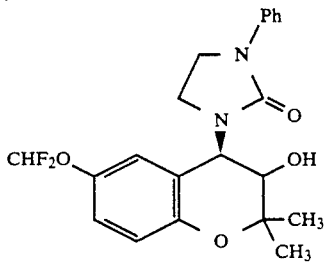

| Example | Method | Reaction time | Yield | m.p. |
|---|---|---|---|---|
| 6-Difluoromethoxy-3,4-dihydro-2,2-dimethyl-trans-4-(1-aza-2-oxo-1-cycloheptyl)-2H-benzo[b]pyran-3-ol 16 | A | 72 h | 20% | 164° C. |

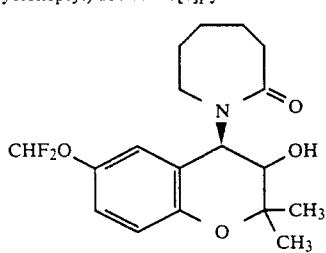

| Example | Method | Reaction time | Yield | m.p. |
|---|---|---|---|---|
| 6-Trifluoromethoxy-3,4-dihydro-2,2-dimethyl-trans-4-(2-oxo-1-pyrrolidinyl)-2H-benzo[b]pyran-3-ol 17 | A | 48 h | 70% | 195-6° C. |

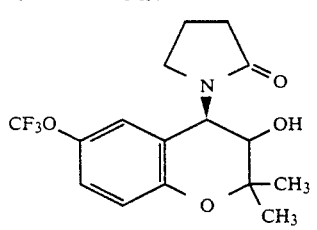

| Example | Method | Reaction time | Yield | m.p. |
|---|---|---|---|---|
| 6-Trifluoromethoxy-3,4-dihydro-2,2-dimethyl-trans-4-(2-oxo-1-piperidinyl)-2H-benzo[b]pyran-3-ol 18 | A | 48 h | 70% | 198-200° C. |

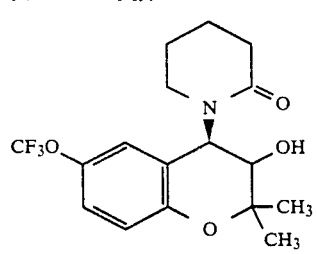

6-Trifluoromethylsulphinyl-3,4-dihydro-2,2-dimethyl-trans-4-(2-oxo-1-piperidinyl)-2H-benzo[b]pyran-3-ol
19 see description

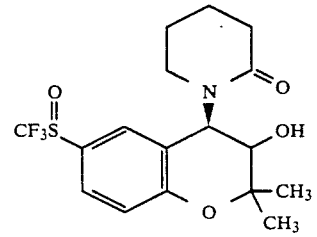

6-Trifluoromethylthio-3,4-dihydro-2,2-dimethyl-trans-4-(2-oxo-1-pyrrolidinyl)-2H-benzo[b]pyran-3-ol

TABLE 1-continued

| Example | | Method | Reaction time | Yield | m.p. |
|---|---|---|---|---|---|
| 20 6-Trifluoromethylthio-3,4-dihydro-2,2-dimethyl-trans-4-(2-oxo-1-piperidinyl)-2H-benzo[b]pyran-3-ol | (structure: CF₃S-benzopyran with 2-oxopyrrolidinyl, OH, 2,2-dimethyl) | A | 72 h | 32% | 198° C. |
| 21 6-Trifluoromethylsulphonyl-3,4-dihydro-2,2-dimethyl-trans-4-(2-oxo-1-piperidinyl)-2H-benzo[b]pyran-3-ol | (structure: CF₃S-benzopyran with 2-oxopiperidinyl, OH, 2,2-dimethyl) | B | 90 h | 11% | 175° C. |
| 22 6-Difluoromethoxy-3,4-dihydro-2,2-dimethyl-trans-4-(2-oxo-4-N-acetyl-piperazin-1-yl)-2H-benzo[b]pyran-3-ol | (structure: CF₃SO₂-benzopyran with 2-oxopiperidinyl, OH, 2,2-dimethyl) | | see description | | |
| 23 6-Difluoromethoxy-3,4-dihydro-2,2-dimethyl-trans-4-(2-oxo-4-piperazin-1-yl)-2H-benzo[b]pyran-3-ol | (structure: CHF₂O-benzopyran with 2-oxo-4-N-acetyl-piperazinyl, OH, 2,2-dimethyl) | | | | 139–140° C. |
| 24 6-Difluoromethoxy-2,2-dimethyl-4-(2-oxo-4-N-isopropyl-piperazin-1-yl)-2H-benzo[b]pyran | (structure: CHF₂O-benzopyran with 2-oxo-4-piperazinyl (NH), OH, 2,2-dimethyl) | | see description | 77% | 240° C. (dec.) |

| Example | | Method | Reaction time | Yield | m.p. |
|---|---|---|---|---|---|
| 25 | (structure: 6-difluoromethoxy chromene with N-isopropylpiperazinone substituent) | B | 65 h | 0.8% | above 260° C. |

6-Difluoromethoxy-3,4-dihydro-2,2-dimethyl-trans-4-(2-oxo-3-thiazolidin-1-yl)-2H-benzo[b]pyran-3-ol

| 26 | (structure: chromanol with 2-oxo-thiazolidinyl) | B | 72 h | 5% | 168–180° C. |

6-Difluoromethoxy-2,2-dimethyl-4-(2-oxo-3-thiazolidin-1-yl)-2H-benzo[b]pyran

| 27 | (structure: chromene with 2-oxo-thiazolidinyl) | B | 72 h | 1% | |

6-Difluoromethoxy-3,4-dihydro-2,2-dimethyl-trans-4-(2-oxo-4-N-benzylpiperazin-1-yl)-2H-benzo[b]pyran-3-ol

| 28 | (structure: chromanol with N-benzylpiperazinone) | A | 72 h | 34% | 130–2° C. |

6-Difluoromethoxy-3,4-dihydro-2,2-dimethyl-trans-4-(2-cyanimino-3-imidazolidin-1-yl)-2H-benzo[b]pyran-3-ol

| 29 | (structure: chromanol with cyanimino-imidazolidinyl) | B | 48 h | 28% | 243–4° C. |

6-Difluoromethoxy-3,4-dihydro-2,2-dimethyl-trans-4-(2-oxo-4-N-isopropylpiperazin-1-yl)-2H-benzo[b]pyran-3-ol

TABLE 1-continued

| Example | | Method | Reaction time | Yield | m.p. |
|---|---|---|---|---|---|
| 30 | [structure: 4-(4-isopropyl-2-oxopiperazin-1-yl) chromanol with CHF₂O substituent, OH, and gem-dimethyl] | B | 65 h | 29% | 167–169° C. |

6-Trifluoromethoxy-2,2-dimethyl-4-(2-oxo-1-pyrrolidinyl)-2H-benzo[b]pyran

| 31 | [structure: 2H-benzo[b]pyran with CF₃O and 2-oxopyrrolidinyl substituent] | B | 48 h | 3% | oil |

6-Trifluoromethylsulphonyl-3,4-dihydro-2,2-dimethyl-trans-4-(2-oxo-1-pyrrolidinyl)-2H-benzo[b]pytran-3-ol

| 32 | [structure: chromanol with CF₃SO₂ substituent, 2-oxopyrrolidinyl, OH, and gem-dimethyl] | | see description | | 208° C. |

6-Trifluoromethoxy-2,2-dimethyl-4-(2-oxo-1-piperidinyl)-2H-benzo[b]pyran

| 33 | [structure: 2H-benzo[b]pyran with CF₃O and 2-oxopiperidinyl substituent] | A | 48 h | 3% | 200–201° C. |

6-Difluoromethoxy-2,2-dimethyl-4-(2-oxo-3-N-methyl-hexahydropyrimidin-1-yl)-2H-benzo[b]pyran

| 34 | [structure: 2H-benzo[b]pyran with CHF₂O and 2-oxo-3-N-methyl-hexahydropyrimidinyl substituent] | B | 48 h | 3% | oil |

6-Trifluoromethoxy-3,4-dihydro-2,2-dimethyl-trans-4-(2-oxo-4-N-benzylpiperazin-1-yl)-2H-benzo[b]pyran-3-ol TABLE 1-continued

| Example | | Method | Reaction time | Yield | m.p. |
|---|---|---|---|---|---|
| 35 | Ph-CH2-N(piperazinone)-N-[CF3O-chroman-4-yl, 3-OH, 2,2-diMe] | B | 70 h | 30% | 140–142° C. |

6-Trifluoromethoxy-2,2-dimethyl-4-(2-oxo-4-N-benzylpiperazin-1-yl)-2H-benzo[b]pyran

| 36 | Ph-CH2-N(piperazinone)-N-[CF3O-2H-chromene-4-yl, 2,2-diMe] | B | 70 h | 2% | oil |

6-Trifluoromethoxy-3,4-dihydro-2,2-dimethyl-trans-4-(2-oxo-4-piperazin-1-yl)-2H-benzo[b]pyran-3-ol

| 37 | H-N(piperazinone)-N-[CF3O-chroman-4-yl, 3-OH, 2,2-diMe] | A | 16 h | 78% | 249–251° C. |

6-Trifluoromethoxy-3,4-dihydro-2,2-dimethyl-trans-4-(2-oxo-4-N-acetyl-piperidin-1-yl)-2H-benzo[b]pyran-3-ol

| 38 | COCH3-N(piperazinone)-N-[CF3O-chroman-4-yl, 3-OH, 2,2-diMe] | B | 70 h | 71% | 100–103° C. |

6-Trifluoromethylthio-3,4-dihydro-2,2-dimethyl-trans-4-(2-oxo-4-N-benzylpiperazin-1-yl)-2H-benzo[b]pyran-3-ol

| 39 | Ph-CH2-N(piperazinone)-N-[CF3S-chroman-4-yl, 3-OH, 2,2-diMe] | B | 20 h | 41% | 168° C. |

TABLE 1-continued

| Example | Method | Reaction time | Yield | m.p. |
|---|---|---|---|---|
| 6-Difluoromethoxy-3,4-dihydro-2,2-dimethyl-trans-4-(2-oxo-4-N-methylpiperazin-1-yl)-2H-benzo[b]pyran-3-ol<br>40 | B | 66 h | 46% | 150–151° C. |
| 6-Difluoromethoxy-2,2-dimethyl-4-(2-oxo-1-pyrrolidinyl)-2H-benzo[b]pyran<br>41 | B | 50 h | 0.5% | oil |
| 6-Trifluoromethoxy-3,4-dihydro-2,2-dimethyl-trans-4-(2-oxo-4-N-cyclopropylmethyl-ipierazin-1-yl)-2H-benzo[b]pyran-3-o]<br>42 | B | 65 h | 43% | 103–105° C. |
| 6-Difluoromethoxy-2,2-dimethyl-4-2-oxo-4-N-cyclopropyl-methyl-piperazin-1-yl)-2H-benzo[b]pyran<br>43 | B | 65 h | 5% | 193–199° C. |
| 6-Trifluoromethylsulphinyl-3,4-dihydro-2,2-dimethyl-trans-4-(2-oxo-1-pyrrolidinyl)-2H-benzo[b]pyran-3-ol<br>44 | | see description | | oil |

TABLE 1-continued

| Example | Method | Reaction time | Yield | m.p. |
|---|---|---|---|---|
| 6-Trifluoromethoxy-3,4-dihydro-2,2-dimethyl-trans-4-(2-oxo-4-N-methoxycarbonyl-piperazin-1-yl)-2H-benzo[b]pyran-3-ol 45 | A | 70 h | 84% | 140–141° C. |
| 6-Cyano-3,4-dihydro-2,2-dimethyl-trans-4-(2-nitromethylidene-3-imidazolidin-1-yl)-2H-benzo[b]pyran-3-ol 46 | B | 24 h | 11% | >240° C. |
| 6-Trifluoromethylthio-3,4-dihydro-2,2-dimethyl-trans-4-(2-nitromethylidene-3-imidazolidin-1-yl)-2H-benzo[b]pyran-3-ol 47 | A | 72 h | 15% | 237° C. |
| 6-Trifluoromethylthio-3,4-dihydro-2,2-dimethyl-trans-4-(2-cyanimino-3-imidazolidin-1-yl)-2H-benzo[b]pyran-3-ol 48 | A | 16 h | 23% | 205° C. (dec.) |

Example 1'

4-Trifluoromethylsulphonylphenol

Method A'

1 g (5.2 mmol) of 4-trifluoromethylthiophenol are dissolved in 20 ml of methanol and a suspension of 9.6 g of Oxone ® in 20 ml of water is added at 0° C. with stirring. After stirring for 5 days at room temperature, the mixture is diluted using 50 ml of water and extracted using chloroform (3×50 ml). After drying and evaporating, 1.1 g of colorless crystals of 4-trifluoromethylsulphonylphenol remain (94 % of theory) M+ = 226 (8).

Method B'

1 g (5.2 mmol) of 4-trifluoromethylthiophenol is stirred for 20 hours at 50° C. together with 4 ml of glacial acetic acid and 4 ml of 30 % strength hydrogen peroxide, then 2 ml of 30 % strength hydrogen peroxide are added once again and, after a further 2 hours at 50° C., the mixture is worked up as in A'. After chromatography on silica gel, 230 mg of colorless crystals of 4-trifluoromethylsulphonylphenol are obtained (20 % of theory) m.p. 123° C. (lit.: 119°–120° C.)

Example 2'

4-Difluoromethylsulphonylphenol

The compound is accessible analogously to the process described under 1', A' or 1', B'.

Example 3′

4-(2,2,2-Trifluoroethylsulphonyl)phenol

The compound is obtainable analogously to process 1′, A′ or 1′, B′.

Example 4′

6-Trifluoromethylthio-2,2-dimethyl-2H-benzo(b)pyran a)
3-(4-(Trifluoromethylthio)-phenoxy)-3-methyl-1-butyne 13.8 g (0.1 mol) of dried potassium carbonate and 1.6 g (0.01 mol) of potassium iodide are suspended in a solution of 19.4 g (0.1 mol) of 4-(trifluoromethylthio)-phenol in 250 ml of dry butanone and 15.4 g (0.15 mol) of 3-chloro-3-methyl-1-butyne are added dropwise. The mixture is then heated under reflux with stirring for 20 hours, 15.4 g of 3-chloro-3-methyl-1-butyne and 13.8 g of potassium carbonate are added once again and the mixture is further heated under reflux for 40 hours. Inorganic constituents are filtered off, the solution is concentrated, and the residue is taken up in 200 ml of methylene chloride and extracted using 1 N NaOH solution. The organic phase is washed with water, dried and concentrated, and the residue is filtered through silica gel.

Yield: 22 g (85 % of theory)

b)
6-Trifluoromethylthio-2,2-dimethyl-2H-benzo(b)pyran 22 g (0.085 mol) of the previously (4′a) described compound are heated to 180° C under argon for 2 hours in 50 ml of 1,2-dichlorobenzene and then fractionated in vacuo.

Yield: 13 g of colorless oil (59.1 % of theory) b.p. 55° C./2 Pa

Example 5′

6-Trifluoromethylsulphonyl-2,2-dimethyl-2H-benzo(b)-pyran 1 g (4.4 mmol) of 4-trifluoromethylsulphonylphenol are stirred under argon at 80°–90° C. for 20 hours together with 0.66 g of potassium carbonate, 80 mg of potassium iodide and 2 g of 3-chloro-3-methyl-1-butyne in 13 ml of dry butanone. 0.33 g of potassium carbonate, 40 mg of potassium iodide and 1 g of 3-chloro-3-methyl-1-butyne are then added once again and the mixture is stirred at 80°–90° C. for a further 20 hours. It is then allowed to cool and is filtered, and the filtrate is evaporated. The residue is taken up in 20 ml of methylene chloride, washed with water (2×20 ml), dried and evaporated. The oil which remains (1.3 g) is heated under argon to 180° C. for 3 hours in o-dichlorobenzene (3 ml). After distilling off the solvent, the residue is chromatographed on silica gel. 0.5 g of colorless oil are obtained (50 % of theory). $M^+ = 292$ (5).

Example 6′

6-Trifluoromethoxy-2,2-dimethyl-2H-benzo(b)pyran 69.2 g (0.5 mol)of dried potassium carbonate and 8.3 g (0.05 mol) of potassium iodide are suspended in a solution of 90 g (0.5 mol) of 4-trifluoromethoxyphenol in 900 ml of dry acetone and 70 g (0.68 mol) of 3-chloro-3-methyl-1-butyne are added dropwise. After stirring for 36 hours at reflux temperature, 35 g (0.34 mol) of 3-chloro-3-methyl-1-butyne are added once again and the mixture is stirred at reflux temperature for a further 36 hours. The cooled suspension is filtered and washed with acetone, the filtrate is concentrated, the residue is taken up in methylene chloride and the solution is extracted using 1N NaOH solution. The methylene chloride phase is washed until neutral, dried and evaporated.

Yield: 67 g (54.9 % of theory).

67 g of the preceding compound are heated to 180° C. for 4 hours in 380 ml of 1,2-dichlorobenzene. Fractionation in vacuo gives the desired product.

Yield: 45 g (67.2 % of theory) b.p.: 75°–80° C./1.3 Pa.

Example 7′

6-Trifluoromethylsulphinyl-2,2-dimethyl-2H-benzo(b)-pyran a) 2 g (7.7 mmol) of 6-trifluoromethylthio-2,2-dimethyl-2H-benzo(b)pyran (Example 4′) are dissolved in 40 ml of methanol and a suspension of 14.2 g (23.1 mmol) of Oxone ® in 40 ml of water is added at 0° C. After stirring for 2 days at room temperature, the mixture is diluted using 50 ml of water, extracted using chloroform (3×100 ml) and the residue which remains after drying and evaporating is chromatographed on silica gel. 1 g of colorless oil is obtained (47 % of theory) $M^+ = 276$ (9).

b)
6-Trifluoromethylsulphonyl-2,2-dimethyl-2H-benzo(b)-pyran 2 g (7.7 mmol) of 6-trifluoromethylthio-2,2-dimethyl-2H-benzo(b)pyran are stirred at room temperature for 6 days together with 6 ml of glacial acetic acid and 6 ml of 30 % strength hydrogen peroxide, then the mixture is diluted to 100 ml using water and extracted using chloroform (3×70 ml). After drying and evaporating, 2 g of colorless oil remain. By means of HPLC (eluent 98:2 chloroform:methanol), 0.3 g of colorless oil of 6-trifluoromethylsulphinyl-2,2-dimethyl-2H-benzo(b)pyran (14 % of theory) and 0.2 g of colorless oil of 8-trifluoromethylsulphonyl-2,2-dimethyl-2H-benzo(b)pyran (9 % of theory) are obtained.

Example 8′

6-Difluoromethylsulphinyl-2,2-dimethyl-2H-benzo(b)-pyran and

Example 9′

6-(2,2,2-Trifluoroethylsulphinyl-2,2-dimethyl-2H-benzo(b)pyran
were obtained analogously.

Other 6-substituted 2H-benzo(b)pyrans of the general formula V are prepared analogously.

Example 10′

6-Trifluoromethylthio-3,4-dihydro-3-bromo-2,2-dimethyl-2H-benzo(b)pyran-4-ol 7.7 g (0.043 mol) of N-bromosuccinimide are added at 20°–25° C. to a solution of 7 g (0.027 mol) of the benzopyran described previously (Example 4,b) in 60 ml of DMSO and 1 ml of water. After stirring for one hour, the mixture is added to ice and extracted using ethyl acetate (3×100 ml). The combined organic phases were washed with water (3×50 ml), dried and concentrated, whereupon the product crystallizes out.

Yield: 8 g (83 % of theory) of slightly brownish crystals.

Example 11'

6-Trifluoromethylthio-3,4-dihydro-3,4-oxiranyl-2,2-dimethyl-2H-benzo(b)pyran

Oil-free sodium hydride (3.5 g, 80 %, in paraffin oil) are added in portions under nitrogen to a solution of 32 g (0.09 mol) of the bromohydrin described previously in 500 ml of dry tetrahydrofuran. After stirring for one hour at room temperature, 1 g of sodium hydride is added once more. After stirring for a further hour, the mixture is filtered through silica gel and the solution is evaporated.

Yield: 26 g (100 % of theory).

Example 12'

6-Trifluoromethylsulphinyl-3,4-dihydro-2,2-dimethyl-3-bromo-2H-benzo(b)pyran-4-ol 51 g (28.6 mmol) of N-bromosuccinimide are added at 20°–25° C. to a solution of 5 g (18 mmol) of 6-trifluoromethylsulphinyl-2,2-dimethyl-2H-benzo(b)pyran in 45 ml of DMSO and 0.7 ml of water. After stirring for one hour, the mixture is added to ice and extracted using ethyl acetate (3×100 ml). The combined organic phases are washed with water (3×50 ml), dried and concentrated, whereupon the product crystallizes out.

Yield 6.1 g (90 % of theory) of pale brown crystals.

Example 13'

6-Trifluoromethylsulphinyl-3,4-dihydro-2,2-dimethyl-3,4-oxiranyl-2H-benzo(b)pyran Oil-free sodium hydride (0.58 g, 80 %, in paraffin oil) is added in portions to a solution of 5.6 g (15 mmol) of the bromohydrin described previously in 80 ml of dry tetrahydrofuran. After stirring for one hour at room temperature, 0.2 g of sodium hydride is added once again. After a further hour, the mixture is filtered through silica gel and the solution is evaporated.

Yield: 4.3 g (100 % of theory).

EXAMPLE 14'

Preparation process for compounds of the formula H-E

Method A''

29.2 g (0.2 mol) of dimethyl cyanimidodithiocarbonate in 1000 ml of toluene are added dropwise to 0.2 mol of amino compound and the mixture is boiled under reflux for 6 hours. After cooling, the precipitate is filtered off with suction, recrystallized from acetone and dried.

Method B''

A solution of 0.2 mol of amino compound in 100 ml of methanol is added dropwise with stirring to a solution of 47.6 g (0.2 mol) of diphenyl cyanimidocarbonate in 400 ml of methanol and the mixture is heated to boiling for 10 minutes. The residue which remains after evaporating is triturated with ether, filtered off with suction and dried.

The compounds indicated in the table were obtained analogously:

| Starting compound: N₂N—(CH₂)$_p$—Y H-E | | | |
|---|---|---|---|
| p | Y | Yield % (H-E) | Method |
| 2 | N—CH₃ | 44 | A |
| 2 | N—C₆H₅ | 28* | A |
| 3 | N—H | 67 | A |
| 2 | NH | 52 | A |
| 2 | O | 60 | B |
| 2 | S | 67 | B |

*cyclization by reaction with sodium hydride

EXAMPLE 46

Preparation of tablets and capsules

Tablets and capsules which contain the constituents indicated below are prepared by known procedures. These are suitable for the treatment of the diseases previously mentioned, in particular hypertonia, in dosage amounts of in each case one tablet or capsule once daily.

| Constituents | Weight (mg) | |
|---|---|---|
| | Tablet | Capsule |
| 6-Trifluoromethylthio-3,4-dihydro-2,2-dimethyl-trans-4-(2-oxo-1-piperidinyl)-2H-benzo(b)pyran-3-ol | 0.2 | 0.1 |
| Tragacanth | 10 | |
| Lactose | 247.5 | 300 |
| Maize starch | 25 | |
| Talc | 15 | |
| Magnesium stearate | 2.5 | |

EXAMPLE 47

Preparation of ampoules

Ampoules which contain the constituents mentioned in the following can be prepared in a known manner. The active compound is dissolved in water and 1,2-propanediol and the solution is poured into glass ampoules under nitrogen.

| | |
|---|---|
| 6-Trifluoromethylsulphonyl-3,4-dihydro-2,2-dimethyl-trans-4-(2-oxo-1-pyrrolidinyl)-2H-benzo(b)pyran-3-ol | 0.02 mg |
| 1,2-Propanediol | 0.8 ml |
| distilled water to | 2.0 ml |

We claim:

1. A benzopyran of the formula I

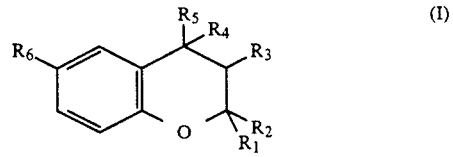

in which
R₁ and R₂ which may be identical or different, denote hydrogen, C₁₋₆-alkyl, C₃₋₆-branched alkyl, C₃₋₇-cycloalkyl or, together with the carbon atom enclosed by them, denote C₃₋₇-spiroalkyl,
R₃ denotes hydroxyl, C₁₋₈-alkoxy, formyloxy, C₁₋₈-alkylcarbonyloxy, C₁₋₈alkoxycarbonyloxy, C₁₋₈-monoalkylaminocarbonyloxy or C₁₋₈-dialkylaminocarbonyloxy, where the C₁₋₈-alkyl or alkoxy groups may both be linear or branched, and R$_4$ stands for hydrogen or
R$_3$ and R$_4$ together form a bond,
R$_5$ denotes a heterocycle of the formula A

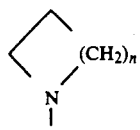
(A)

where n stands for 1,2,3 or 4,
or a heterocycle of the formula B

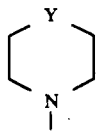
(B)

where Y stands for oxygen, sulphur, unsubstituted amino —NH—, substituted amino —NR$_7$— and R$_7$ denotes straight-chain C$_{1-9}$-alkyl, branched C$_{3-7}$-alkyl, C$_{3-7}$-cycloalkyl, straight-chain or branched C$_{1-9}$-alkyl substituted by C$_{3-7}$-cycloalkyl, C$_{1-8}$-alkylcarbonyl, C$_{1-8}$-alkoxycarbonyl, benzyl, triphenylmethyl, phenyl, benzyloxycarbonyl, phenylcarbonyl or benzylcarbonyl or R$_5$ denotes a heterocycle of the formula C

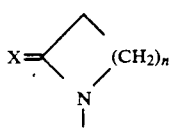
(C)

where X stands for oxygen or sulphur and n stands for 1, 2, 3 or 4
or a heterocycle of the formula D

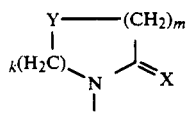
(D)

where m denotes 0, 1 or 2 and k denotes 1, 2 or 3, but in such a way that (m+k) is 1, 2 or 3 and furthermore X and Y have the meaning indicated for the formulae B and C, R$_6$ denotes difluoromethoxy, trifluoromethoxy, trifluoroethoxy, tetrafluoroethoxy, difluoromethylthio, difluoromethylsulphinyl, difluoromethylsulphonyl, trifluoromethylthio, trifluoromethylsulphinyl, trifluoromethylsulphonyl, trifluoroethylthio, trifluoroethylsulphinyl or trifluoroethylsulphonyl, or its pharmaceutically acceptable salt, tautomer or optical isomer.

2. Compound according to claim 1, selected from the group comprising 6-trifluoromethylthiol-3,4-dihydro-2,2-dimethyl-trans-4-(2-oxo-1-pyrrolidinyl)-2H-benzo(b)pyran-3ol, 6-trifluoromethylsulphonyl-3,4-dihydro-2,2-dimethyl-trans-4-(2-oxo-1-pyrrolidinyl)-2H-benzo(b)pyran-3ol, 6-trifluoromethylthio-3,4-dihydro-2,2-dimethyl-trans-4(2-oxo-1-piperidinyl)-2H-benzo(b)-pyran-3-ol, 6-trifluoromethylsulphonyl-3,4-dihydro-2,2-dimethyl-trans-4-(2-oxo-1-piperidinyl)-2H-benzo(b)pyran-3ol, 6-difluoromethoxy-3,4-dihydro-2,2-dimethyl-trans-4-(2-oxo -1-piperidinyl)-2H-benzo(b)pyran-3ol, 6-trifluoromethylthiol-2,2-dimethyl-4-(2-oxo-1-pyrrolidinyl) -2H-benzo(b)pyran, 6-trifluoromethylsulphonyl-2,2-dimethyl-4-(2-oxo-1-pyrrolidinyl) -2H-benzo(b)pyran, 6-trifluoromethylthio-2,2dimethyl-4-(2oxo-1-piperidinyl) -2H-benzo(b)pyran, 6-trifluoromethylsulphonyl-2,2-dimethyl-4-(2-oxo-1-piperidinyl) -2H-benzo(b)pyran, 6-trifluoromethoxy-2,2-dimethyl-4-(2-oxo-1-piperidinyl)-2H-benzo(b)pyran.

3. A compound according to claim 1, wherein R$_3$ and R$_4$ together form a bond.

4. A compound according to claim 2, wherein such compound is 6-trifluoromethylthiol-3,4-dihydro-2,2-dimethyl-trans-4-(2-oxo-1-piperidinyl)-2H-benzo(b) pyran-3-ol.

5. A potassium channel activating composition comprising an amount effective therefor of a compound according to claim 1 and a pharmacologically acceptable diluent.

6. A method of reducing blood pressure in a patient in need thereof which comprises administering to such patient an amount effective therefor of a compound, salt, tautomer or optical isomer according to claim 1.

7. A compound of the formula

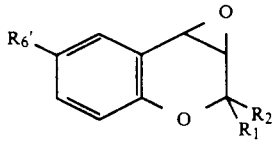
(IIa)

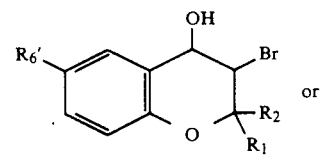
(IIIa)

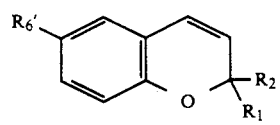
(Va)

in which
R$_1$ and R$_2$ which may be identical or different, denote hydrogen, C$_{1-6}$-alkyl, C$_{3-6}$-branched alkyl, C$_{3-7}$-cycloalkyl or, together with the carbon atom enclosed by them, denote C$_{3-7}$-spiroalkyl, and
R'$_6$ denotes difluoromethoxy, trifluoromethoxy, trifluoroethoxy, tetrafluoroethoxy, difluoromethylthio, difluoromethylsulphinyl, difluoromethylsulphonyl, trifluoromethylthio, trifluoromethylsulphinyl, trifluoromethylsulphonyl, trifluoroethylthio, trifluoroethylsulphinyl or trifluoroethylsulphonyl.

* * * * *